(12) United States Patent
Champagne et al.

(10) Patent No.: US 10,299,523 B2
(45) Date of Patent: May 28, 2019

(54) ERGONOMIC WORK GLOVES

(71) Applicant: Exsomed Holding Company LLC, Scottsdale, AZ (US)

(72) Inventors: Lloyd P. Champagne, Phoenix, AZ (US); Jozef Zoldos, Phoenix, AZ (US)

(73) Assignee: ExsoMed Holding Company, LLC, Phoenix, AZ (US)

( * ) Notice: Subject to any disclaimer, the term of this patent is extended or adjusted under 35 U.S.C. 154(b) by 0 days.

(21) Appl. No.: 15/427,981

(22) Filed: Feb. 8, 2017

(65) Prior Publication Data

US 2017/0143058 A1    May 25, 2017

Related U.S. Application Data

(63) Continuation of application No. 14/542,217, filed on Nov. 14, 2014, now Pat. No. 9,622,523.

(60) Provisional application No. 61/923,953, filed on Jan. 6, 2014.

(51) Int. Cl.
| A41D 19/015 | (2006.01) |
| A41D 19/00 | (2006.01) |
| A41D 13/08 | (2006.01) |
| A41F 1/06 | (2006.01) |
| A61B 42/10 | (2016.01) |

(52) U.S. Cl.
CPC ......... *A41D 19/0096* (2013.01); *A41D 13/08* (2013.01); *A41D 19/0006* (2013.01); *A41D 19/0013* (2013.01); *A41D 19/0058* (2013.01); *A41D 19/015* (2013.01); *A41D 19/01558* (2013.01); *A41F 1/06* (2013.01); *A61B 42/10* (2016.02); *A41D 2400/82* (2013.01); *A41D 2600/10* (2013.01); *A41D 2600/20* (2013.01)

(58) Field of Classification Search
CPC .... A63B 71/148; A61B 19/04; A41D 19/015; A41D 19/00
See application file for complete search history.

(56) References Cited

U.S. PATENT DOCUMENTS

| 467,974 | A | 2/1892 | Healey |
| 723,348 | A | 3/1903 | Wilkins |
| 1,279,855 | A | 9/1918 | Garvey |
| D61,479 | S | 9/1922 | Rice |
| 1,538,262 | A | 5/1925 | Ackerman |
| 1,894,066 | A | 1/1933 | Smith |
| 2,036,413 | A | 4/1936 | Wendell |

(Continued)

FOREIGN PATENT DOCUMENTS

| DE | 654995 | 1/1938 |
| EP | 2828409 | 9/2015 |

(Continued)

OTHER PUBLICATIONS

USPTO; Non-Final Office Action dated May 5, 2017 in U.S. Appl. No. 14/133,424.

(Continued)

*Primary Examiner* — Tejash Patel
(74) *Attorney, Agent, or Firm* — Snell & Wilmer L.L.P.

(57) ABSTRACT

Disclosed is a glove that alleviates the biasing force associated with opening or closing the hand and fingers. In some aspects the glove may have preformed angled portions at one or more joints or locations on the hand to enable the hand to flex between the open and closed position.

32 Claims, 41 Drawing Sheets

(56) References Cited

U.S. PATENT DOCUMENTS

| | | |
|---|---|---|
| D100,816 S | 8/1936 | Fuchs |
| 2,075,550 A | 3/1937 | Smith |
| 2,173,734 A | 9/1939 | Sidnell |
| D133,927 S | 9/1942 | Balzano |
| 2,434,035 A | 1/1948 | De Laney |
| D164,429 S | 9/1951 | Kress |
| D179,250 S | 11/1956 | Higier |
| 2,838,759 A | 6/1958 | William |
| 3,096,523 A | 7/1963 | Bruchas |
| 3,283,338 A | 11/1966 | Lucian |
| 3,601,816 A | 8/1971 | Pordes |
| 3,649,967 A | 3/1972 | Millman |
| 3,728,739 A | 4/1973 | Semp |
| 3,748,792 A | 7/1973 | Lamb |
| 3,789,555 A | 2/1974 | Means |
| 3,867,727 A | 2/1975 | Povlacs |
| 3,872,514 A | 3/1975 | Liebelt |
| 3,872,515 A | 3/1975 | Miner |
| 4,000,524 A | 1/1977 | Rinehart |
| 4,172,293 A | 10/1979 | Vistins |
| 4,218,778 A | 8/1980 | Stansbury |
| 4,441,213 A | 4/1984 | Trumble et al. |
| 4,494,249 A | 1/1985 | Hansson |
| 4,590,626 A | 5/1986 | Chen |
| 4,594,736 A | 6/1986 | Connelly |
| 4,663,783 A | 5/1987 | Obayashi |
| 4,689,832 A | 9/1987 | Mulvaney |
| 4,845,780 A | 7/1989 | Reimers |
| 4,924,530 A | 5/1990 | Tagaya |
| 5,317,759 A | 6/1994 | Pierce |
| 5,323,490 A | 6/1994 | Yarbrough |
| 5,345,612 A | 9/1994 | Stein |
| D359,381 S | 6/1995 | Henriquez |
| 5,442,816 A | 8/1995 | Seketa |
| 5,500,956 A | 3/1996 | Schulkin et al. |
| 5,500,957 A | 3/1996 | Stein |
| 5,527,244 A | 6/1996 | Waller et al. |
| D372,578 S | 8/1996 | Chapman |
| 5,636,382 A | 6/1997 | Chopko et al. |
| 5,644,797 A | 7/1997 | Dabeshvar |
| 5,692,242 A | 12/1997 | Tekerman et al. |
| D391,683 S | 3/1998 | Heringer |
| 5,728,255 A | 3/1998 | Jurrius |
| 5,781,931 A | 7/1998 | Lee |
| 5,794,266 A | 8/1998 | Han |
| 5,817,433 A | 10/1998 | Darras |
| 5,907,870 A | 6/1999 | Monroe et al. |
| 5,946,720 A | 9/1999 | Sauriol |
| 5,965,276 A | 10/1999 | Shlenker et al. |
| 5,983,395 A | 11/1999 | Lei |
| 6,081,928 A | 7/2000 | Bourne |
| 6,272,687 B1 | 8/2001 | Cunningham |
| 6,415,443 B1 * | 7/2002 | Schierenbeck .. A41D 19/01529 2/159 |
| 6,575,822 B2 | 6/2003 | Lowe |
| 6,578,205 B1 | 6/2003 | King |
| D479,972 S | 9/2003 | Cueto |
| 6,732,378 B2 | 5/2004 | Novak |
| 6,760,923 B1 | 7/2004 | Tate |
| 6,779,199 B1 | 8/2004 | O'Dea |
| D512,549 S | 12/2005 | Benjamin |
| 7,234,170 B2 | 6/2007 | Simic |
| D552,827 S | 10/2007 | Muse |
| 7,293,296 B1 | 11/2007 | Beraznik et al. |
| RE40,142 E | 3/2008 | Fous |
| D567,476 S | 4/2008 | Harland |
| D605,377 S | 12/2009 | House |
| 7,694,352 B2 | 4/2010 | Kogawa et al. |
| 7,802,314 B2 | 9/2010 | Cohen |
| 7,802,316 B2 | 9/2010 | Hofmann |
| D628,767 S | 12/2010 | Bengyak |
| 7,856,670 B1 | 12/2010 | Hazuga et al. |
| 8,336,119 B2 | 12/2012 | Phelps |
| D677,030 S | 2/2013 | Wessels |
| 8,400,256 B2 | 3/2013 | Matthews |
| D680,695 S | 4/2013 | Lin et al. |
| 8,453,266 B2 | 6/2013 | Bevier et al. |
| 8,458,815 B1 | 6/2013 | Green |
| 8,505,115 B2 | 8/2013 | Matsuoka |
| 8,512,615 B1 | 8/2013 | Amdur et al. |
| 8,572,765 B2 | 11/2013 | Tao |
| D707,526 S | 6/2014 | Daniel |
| D733,974 S | 7/2015 | Lawton |
| D735,968 S | 8/2015 | Furlong |
| D739,993 S | 10/2015 | Mathota |
| 9,179,718 B2 | 11/2015 | Anstey |
| D747,070 S | 1/2016 | Kelly |
| D754,929 S | 4/2016 | Champagne |
| 9,323,327 B2 | 4/2016 | Aleksov et al. |
| 9,370,209 B2 | 6/2016 | Hull |
| 9,414,630 B2 * | 8/2016 | Schatzberg ............ B29C 41/14 |
| 9,622,523 B2 | 4/2017 | Champagne |
| 9,801,422 B2 * | 10/2017 | Anstey ............... A41D 19/0082 |
| 9,974,611 B2 | 5/2018 | Champagne et al. |
| 10,188,161 B2 | 1/2019 | Champagne |
| 2002/0166156 A1 | 11/2002 | Clark et al. |
| 2004/0255362 A1 | 12/2004 | Soerens et al. |
| 2005/0015846 A1 | 1/2005 | Vistins et al. |
| 2006/0005295 A1 | 1/2006 | Mattesky |
| 2006/0191056 A1 | 8/2006 | Bottcher |
| 2006/0218697 A1 | 10/2006 | Modha et al. |
| 2007/0074331 A1 | 4/2007 | Bitzer |
| 2007/0209097 A1 | 9/2007 | Iacullo |
| 2008/0000010 A1 | 1/2008 | Erickson et al. |
| 2008/0134411 A1 | 6/2008 | Shapiro |
| 2008/0155726 A1 | 7/2008 | Anclien |
| 2008/0244808 A1 | 10/2008 | Chaen |
| 2010/0050311 A1 | 3/2010 | Tsai |
| 2011/0258751 A1 | 10/2011 | Matsuoka |
| 2011/0277215 A1 | 11/2011 | Lee et al. |
| 2011/0296582 A1 | 12/2011 | Bevier et al. |
| 2012/0042437 A1 | 2/2012 | Matthews |
| 2012/0047616 A1 | 3/2012 | Wood |
| 2013/0061369 A1 | 3/2013 | Lim |
| 2013/0263355 A1 | 10/2013 | Mavraganes |
| 2013/0291282 A1 | 11/2013 | Anstey |
| 2014/0020152 A1 | 1/2014 | Yang |
| 2014/0150162 A1 | 6/2014 | Guan |
| 2014/0166521 A1 | 6/2014 | Champagne et al. |
| 2014/0208480 A1 | 7/2014 | Champagne et al. |
| 2014/0208481 A1 | 7/2014 | Champagne et al. |
| 2014/0259283 A1 | 9/2014 | Govindasamy |
| 2015/0189932 A1 | 7/2015 | Champagne et al. |
| 2016/0081408 A1 | 3/2016 | Hull |
| 2016/0174634 A1 | 6/2016 | Schatzberg |
| 2017/0049167 A1 | 2/2017 | Champagne et al. |

FOREIGN PATENT DOCUMENTS

| | | |
|---|---|---|
| EP | 2950739 | 11/2015 |
| FR | 476889 | 9/1915 |
| FR | 1141139 | 8/1957 |
| GB | 2148094 | 5/1985 |
| WO | WO199639055 | 12/1996 |
| WO | WO2013126727 | 8/2013 |

OTHER PUBLICATIONS

USPTO; Non-Final Office Action dated May 8, 2017 in U.S. Appl. No. 14/133,438.

USPTO; Non-Final Office Action dated May 31, 2017 in U.S. Appl. No. 14/099,803.

USPTO; Final Office Action dated Jun. 26, 2017 in U.S. Appl. No. 14/133,424.

USPTO; Final Office Action dated Jun. 28, 2017 in U.S. Appl. No. 14/133,438.

USPTO; Final Office Action dated Jul. 27, 2017 in U.S. Appl. No. 14/099,803.

PCT; International Search Report and Written Opinion dated Feb. 25, 2014 in Application No. PCT/US2013/073727.

PCT; International Search Report and Written Opinion dated Apr. 17, 2014 in Application No. PCT/US2014/013940.

(56) References Cited

OTHER PUBLICATIONS

USPTO; Office Action dated Jun. 17, 2015 in U.S. Appl. No. 14/542,217.
USPTO; Notice of Allowance dated Dec. 10, 2015 is U.S. Appl. No. 29/475,635.
USPTO; Office Action dated May 18, 2016 in U.S. Appl. No. 14/542,217.
USPTO; Restriction Requirement dated May 20, 2016 in U.S. Appl. No. 14/099,803.
USPTO; Restriction Requirement dated Jun. 17, 2016 in U.S. Appl. No. 14/133,424.
USPTO; Non-Final Office Action dated Oct. 21, 2016 in U.S. Appl. No. 14/133,438.
USPTO; Notice of Allowance dated Oct. 24, 2016 in U.S. Appl. No. 29/557,960.
USPTO; Final Office Action dated Dec. 23, 2015 in U.S. Appl. No. 14/542,217.
USPTO; Office Action dated Nov. 2, 2016 in U.S. Appl. No. 14/133,424.
USPTO; Notice of Allowance dated Dec. 19, 2016 in U.S. Appl. No. 14/542,217.
USPTO; Office Action dated Feb. 7, 2017 in U.S. Appl. No. 14/099,803.
USPTO; Final Office Action dated Mar. 21, 2017 in U.S. Appl. No. 14/133,438.
USPTO; Final Office Action dated Mar. 24, 2017 in U.S. Appl. No. 14/133,424.
USPTO; Final Office Action dated Apr. 12, 2017 in U.S. Appl. No. 14/099,803.
USPTO; Advisory Action dated Apr. 12, 2017 in U.S. Appl. No. 14/133,424.
USPTO; Advisory Action dated Apr. 25, 2017 in U.S. Appl. No. 14/133,438.
USPTO; Final Office Action dated Nov. 27, 2017 in U.S. Appl. No. 14/099,803.
USPTO; Non-Final Office Action dated Dec. 27, 2017 in U.S. Appl. No. 14/133,424.
USPTO; Non-Final Office Action dated Jan. 4, 2018 in U.S. Appl. No. 14/133,438.
USPTO; Notice of Allowance dated Jan. 17, 2018 in U.S. Appl. No. 14/099,803.
USPTO; Non-Final Office Action dated Sep. 26, 2017 in U.S. Appl. No. 14/099,803.
USPTO; Final Office Action dated Feb. 9, 2018 in U.S. Appl. No. 14/133,438.
USPTO; Notice of Allowance dated Feb. 15, 2018 in U.S. Appl. No. 14/099,803.
USPTO; Final Office Action dated Feb. 28, 2018 in U.S. Appl. No. 14/133,424.
USPTO; Advisory Action dated Apr. 17, 2018 in U.S. Appl. No. 14/133,438.
USPTO; Advisory Action dated Apr. 18, 2018 in U.S. Appl. No. 14/133,424.
USPTO; Non-Final Office Action dated Apr. 20, 2018 in U.S. Appl. No. 15/222,883.
USPTO; Notice of Allowance dated Sep. 19, 2018 in U.S. Appl. No. 15/222,883.
AU; Examination Report dated Jul. 26, 2018 in Application No. 2014212306.
EP; Examination Report dated Jun. 26, 2018 in Application No. 13811723.9.
EP: Intent to Grant dated Dec. 14, 2018 in Application No. EP13811723.9.

* cited by examiner

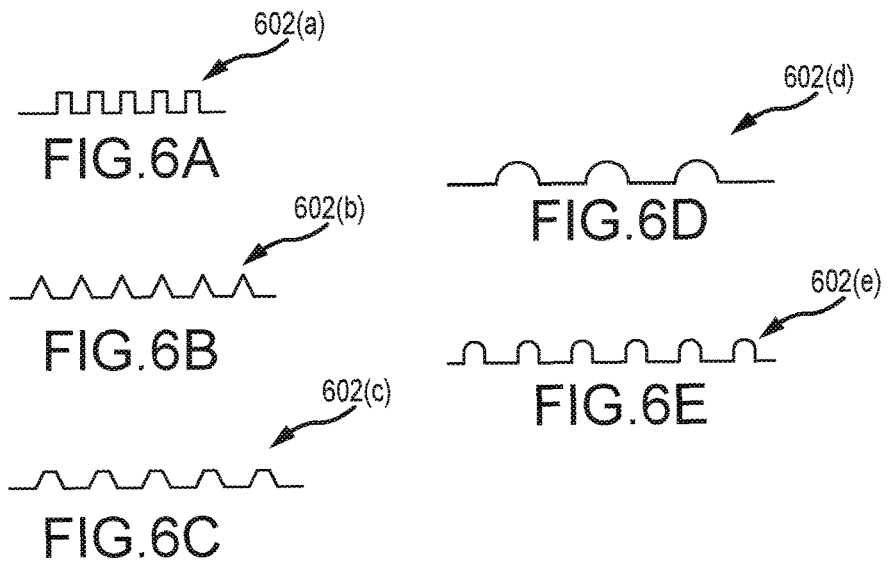
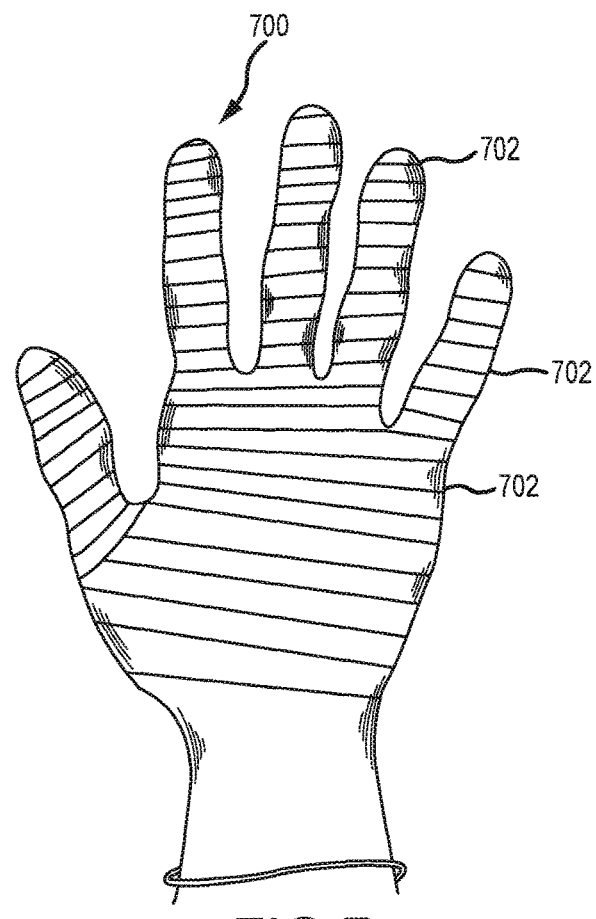

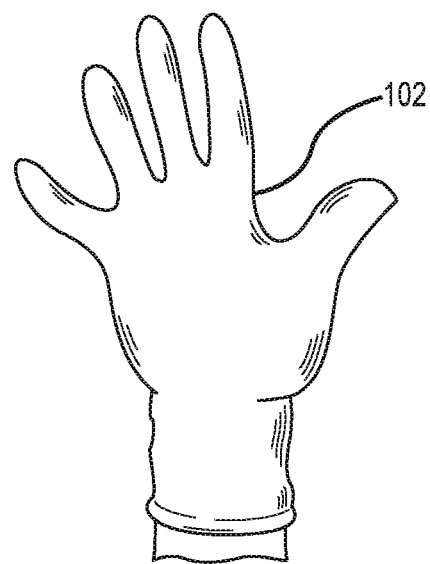
FIG.12
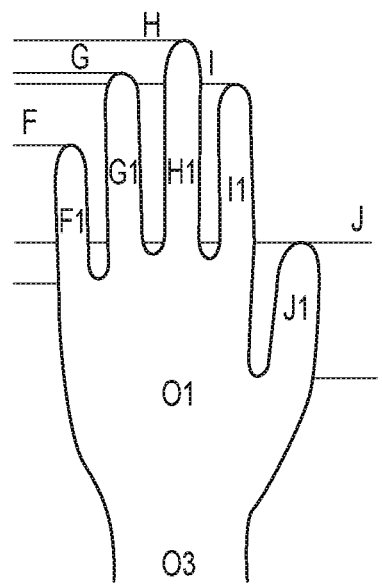 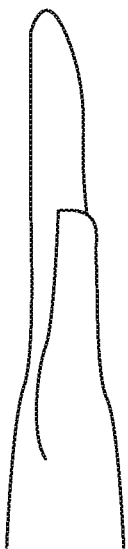
FIG.13A    FIG.13B

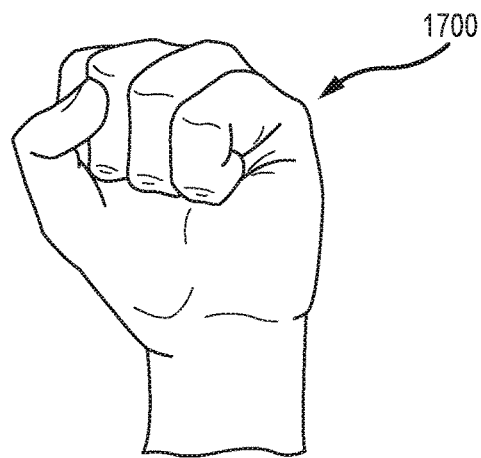
FIG.17
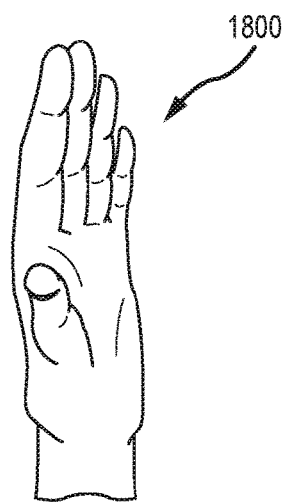 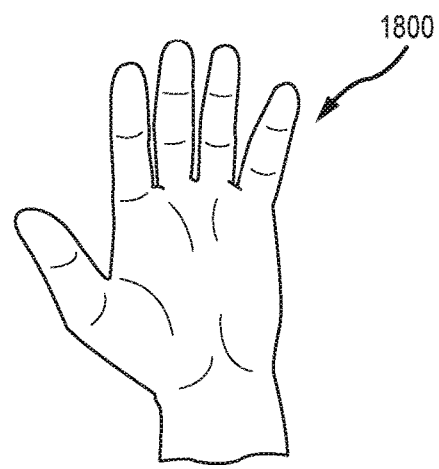
FIG.18A FIG.18B

INCISION

ERGONOMIC WORK GLOVES

CROSS REFERENCE TO RELATED APPLICATION

This application is a continuation of U.S. application Ser. No. 14/542,217, filed on Nov. 14, 2014 and claims priority to U.S. Provisional Patent Application No. 61/923,953 filed on Jan. 6, 2014, the respective disclosure of which is incorporated by reference in its entirety.

FIELD OF THE INVENTION

The present invention relates to a glove formed to be all or partially in essentially the relaxed shape of a human hand, potentially including being formed in a flexed position at one or more of the finger joints, palm and/or dorsum of the hand. The invention also relates to other features of a glove to alleviate biasing forces related to movement of the hand and to assist the glove in conforming to the movement of the hand and/or to make a glove better suited for use in a given application.

BACKGROUND OF THE INVENTION

Gloves, including work gloves, are known in the art. The gloves are usually manufactured from cloth, leather or rubber and are suited to protect the hand to some degree. Most gloves are formed in a shape approximately the same as a hand when pressed flat on a surface or extended to be essentially flat or straight, such as shown in FIG. 1 and FIG. 2. In that position, the fingers extend outward, essentially straight from the palm (in this context "straight" means there is essentially no bend at any of the joints). In this position, the thumb is oriented in a flat plane or is slightly abducted away from the palm. A problem with the standard glove shape is that the relaxed hand is not naturally in a flat position with the fingers essentially straight. As shown in FIGS. 3-4, 21 and 30A-30B, when in its normal, relaxed position, which is also called the normal hand cascade position, the joints of the fingers (the fingers and thumb also collectively referred to herein as "digits") are naturally in a flexed position, with the thumb in a different plane than the fingers. This normal position does not match the shape of a standard surgical glove.

If a person wears gloves for a long period, his/her fingers and hands can become tired or fatigued because of constantly overcoming the biasing forces of the gloves in order to flex the fingers and hands (either to a closed position, open position, or both).

Consequently, when a standard work glove is placed on a hand, the material of the glove tends to hold the fingers from the normal, relaxed position to the less natural straight position. When a worker then uses his/her hand, in order to flex the fingers, the biasing force of the glove material must be overcome. For example, FIG. 5 shows a hand 500 grasping a dental instrument 502, FIG. 33 shows a hand grasping a screw in a three-point chuck pinch, and FIG. 34 shows a hand grasping a device using the three ulnar digits and thumb. In FIG. 5, fingers 504-510 are flexed to grasp the instrument 502, and to do so, any resistance by glove 512 must be overcome. The same is true when moving the hand to the positions in FIG. 33 or 34.

In addition to standard gloves being formed in essentially a straight position, they have no structure to permit the expansion or contraction of the dimensions of portions of the hand when the hand is moved to a closed or open position. For example, the circumference of a flexed finger (such as when the fingers are flexed towards the palm of the hand) is greater than its circumference when relaxed or in the straight position. This concept is illustrated in FIGS. 22 and 37, showing a 20% increase in circumference in a female index finger and a 22% increase in circumference in a male index finger. If gloves are designed so they tightly fit fingers that are in the straight position, and then the fingers are flexed, the fingers must also overcome the biasing force of the glove material that restricts digital expansion. Consequently, there is a need for extra material during flexion of the fingers so the portion of the glove covering the portion of the finger that expands can (1) permit expansion when the finger is flexed, and (2) contract back into shape and is not used when the finger is not flexed. The biasing force of gloves also includes adduction of the fingers, a force tending to keep the fingers together in line rather than in their natural cascading position. This is another biasing force that must be overcome when using standard gloves.

Glove designs with baggy, or loose-fitting portions, at one or more areas are known, but such gloves are not optimal for a worker performing procedures that require fine, precise work. Further, baggy gloves may become caught in pinch points or machinery. FIG. 31 depicts an oversized glove on a hand and shows how the excess material can create problems with manual dexterity, slippage, and getting caught in pinch points or machinery.

Glove designs are also known that have ribs at some areas, but while the ribs may help to some degree, they do not overcome the problems described herein.

It would be beneficial to have gloves that minimize biasing forces, that include a minimal amount of excess, loose or baggy material, and that are relatively simple to manufacture, so they are cost effective.

SUMMARY OF THE INVENTION

Aspects of the present invention are gloves (referred to herein as "work gloves" or "gloves") that utilize shapes with the finger portions and thumb positioned more towards their natural, relaxed position. Preferably, the gloves reduce the biasing force inherent in standard gloves when (1) closing the hand, (2) opening the hand, and (3) closing and/or opening the fingers and/or moving the thumb. As set forth in more detail below, a glove according to the invention may also be combined with, or instead include: (a) relaxing or distressing features (also referred to as "patterns") at one or more positions, (b) thinner portions of material at one or more positions, and/or (c) different materials with different flexibility characteristics at one or more positions.

A glove according to the invention typically includes either (1) a single material that is suitable to provide enough protection and flexibility to provide the claimed features, or (2) a plurality of materials wherein one or more materials provides protection for the hand and one or more others provides the necessary flexibility, as described herein. For example, this flexible, protective material, such as cloth or leather, may be used to manufacture the glove except for one or more of (a) the spaces between any set, or multiple sets, of fingers, (b) the space between the thumb and index finger, (c) at one or more joints of the finger and/or thumb, (d) the center region of the palm, (d) the tops of the fingers, (e) all or part of the dorsum of the hand, (f) the space between one or more finger MCP joints and PIP joints, and/or (g) the space between the thumb PIP joint and IP joint. Additionally, any of the flexible material portions of a glove may include intermittent harder materials, providing as, for example, intermittent square, triangular, round, rectangular or other shapes that assist in protecting the hand.

A glove according to aspects of the invention may also have a zig-zag, rather than a straight, stitching pattern along one or more of the seams if the seams are stitched. Additionally, flexible threading, comprised of natural or synthetic rubber, or a flexible plastic, or any suitable material, may be used to stitch one or more seams to increase flexibility.

Exemplary gloves may be essentially formed either partially or entirely in the approximate shape of a relaxed hand, examples of which are shown in FIGS. 3, 4, 21, 30A and 30B. Because of the glove's shape, the amount of biasing force that must be overcome to flex the fingers, move the thumb, close the hand, and/or move the thumb to a position where it is pressed against one of the fingers is reduced. A person can therefore utilize the gloves for longer periods without his/her fingers or hands becoming as tired or fatigued as when using conventional gloves.

A glove according to various embodiments of the invention may be made with pre-formed angles (also referred to herein as "flex angles") at one or more of the metacarpophalangeal (MCP) joints, proximal interphalangeal (PIP) joints and distal interphalangeal (DIP) joints in the fingers, and/or elsewhere. Some examples of flex angles are shown in FIGS. 3-4 and 21. In one example, one or more of the portions of the glove corresponding to the MCP joints may be formed at a flex angle, and/or one or more of the portions of the glove corresponding to the PIP joints may be formed at a flex angle, and/or one or more of the portions of the glove corresponding to the DIP joints may be formed at a flex angle. Any combination or permutation of glove portions corresponding to any combination of joints on any combination of fingers and/or the thumb and/or the palm can include a flex angle as described herein.

In accordance with further examples, MCP joint portions of a glove have a greater flex angle than the PIP and DIP positions to render a glove that more closely replicates the natural, cascading position of the fingers and permits the hand to be in an open, usable position as shown, for example, in FIG. 21.

Additionally, the portion of the glove that retains the thumb may have portions at the thumb MCP and IP joints that are formed at respective flex angles, corresponding to essentially the angle of the relaxed position of the thumb. Further, the overall position of the thumb portion of the glove may be essentially in the thumb's natural, relaxed position, e.g., that of abduction from the palm with some flexion at the MCP and IP joints.

Exemplary gloves can include a texturing or patterning, or other design features, such as patterns, ripples, ribs, textures or bumps, or a combination thereof (collectively, "pattern" or "patterns") formed as part of the glove; such pattern making the glove easier to flex when the hand is opened and/or closed. The patterns provide extra material, which is used when a hand or digit flexes in a certain manner and alleviate the need for oversized glove portions. These patterns can be formed on the outer and/or inner surface of the glove, and are preferably on the outer (or outside) surface.

Patterns can be added to any relevant portion of a glove according to aspects of the invention. As one example, a glove as described herein can include longitudinal ribs along parts of one or more fingers or the thumb to allow for expansion of the digit (i.e., an increase in circumference during flexing). Furthermore, a pattern can exist in one or more spaces between the fingers, or the thumb and index finger, or the thumb and index finger, thus reducing the biasing force of the glove in that area(s) and allowing easier abduction or movement. Also, if the glove is formed with flex angles, it may have a bias toward flexion, rather than extension (the opening of the hand), so features can be added on the palm side of the glove, such as at the thumb, and/or one or more finger creases and/or center of the palm to relieve some of the force of opening or closing the hand and/or digits.

Further, exemplary gloves can include patterns and/or shapes at any suitable location, including at the joint portions including the flex angles, to reduce the biasing force to close and/or open the hand.

In accordance with further exemplary embodiments, a glove may include material of various thicknesses. For example, a glove can include material of a first thickness corresponding to most of the hand, and have material that is thinner at the portions of the hand (which includes the digits) that flex when opening or closing, e.g., at one or more joints of the digits and/or on the dorsum or palm. Thinner material may also, or instead, be used at locations where greater tactile sensation is desired.

In accordance with yet further exemplary embodiments, a glove includes material in some areas that is more flexible in areas where the digits and/or hand flex, and may include another material that is more puncture resistant than the glove material in other areas. For example, the glove can include reinforced material on the fingertips and/or palm areas and a second material that flexes more at one or more of the joints and/or the dorsum or palm. Alternatively, the glove can include a thinner material, whether flexible or not, at one or more finger tips to allow for better tactile signals when performing fine work. Additionally, a glove according to the invention may have sensory enhancers, such as a hardened material formed in any suitable shape and size to enhance tactile sensation. Such enhancers may be hardened ridges, ball bearings or other areas that are formed of a relatively hard material to enable the force associated with touching an object to be transmitted to a portion of the hand, such as a fingertip. In this manner, tactile perception is increased even if the glove material is relatively thick.

Gloves in accordance with the present disclosure can also include any combination of materials, flex angles, patterns, and features as described herein.

As set forth in more detail below, various gloves as described herein can accommodate the movement of the hand and digits with reduced biasing force, and at the same time fit properly (and preferably not be oversized or baggy). Additionally, gloves as described herein may increase tactile sensitivity during use.

BRIEF DESCRIPTION OF THE DRAWINGS

FIG. 6A is a close-up, side illustration of an exemplary pattern suitable for the material of the glove of FIG. 6.

FIG. 6B is a close-up, side illustration of another exemplary pattern suitable for the material of the glove of FIG. 6.

FIG. 6C is a close-up, side illustration of another exemplary pattern suitable for the material of the glove of FIG. 6.

FIG. 6D is a close-up, side illustration of another exemplary pattern suitable for the material of the glove of FIG. 6.

FIG. 6E is a close-up, side illustration of another pattern suitable for the material of the glove of FIG. 6.

FIG. 7 depicts a top view (wherein the flex angles of the joints cannot be readily seen) of an exemplary glove that includes a pattern of ribs.

FIG. 12 illustrates a hand with a standard glove wherein the hand is biased to flexion.

FIG. 13A illustrates a palm view of a standard glove.

FIG. 13B illustrates a side view of the glove of FIG. 13A.

FIG. 17 illustrates a hand without a glove, wherein the hand is fully biased to the flexion position.

FIG. 18A illustrates a side view of a hand in the straight position, which is the position in which most current gloves are formed.

FIG. 18B illustrates a palm view of the hand of FIG. 18A.

DETAILED DESCRIPTION OF PREFERRED EMBODIMENTS

Figure 1:
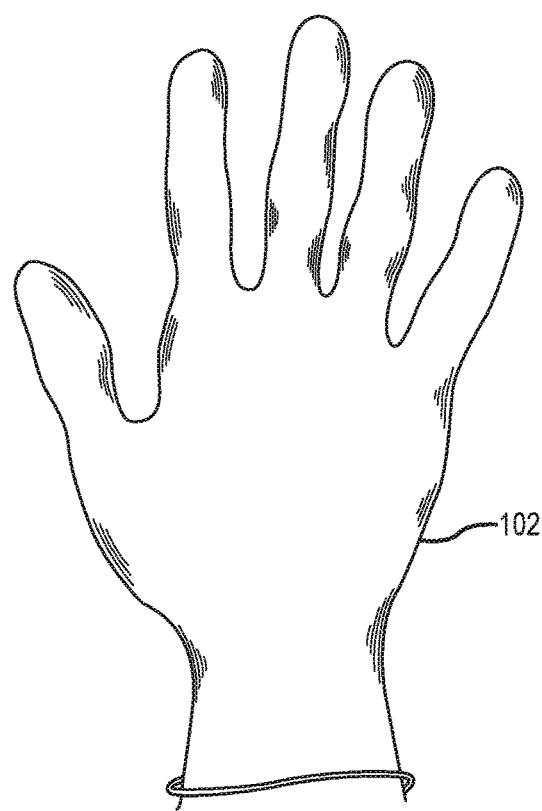
FIG. 1 depicts a hand that is flat with the fingers extending outward from the palm in essentially a straight position, with a glove on the hand.
Figure 2:
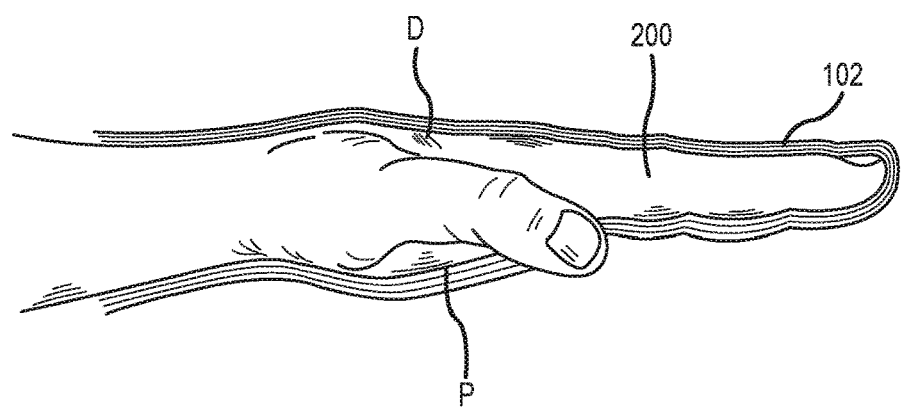
FIG. 2 depicts a partial cross-sectional view of the glove of FIG. 1.
Figure 3:
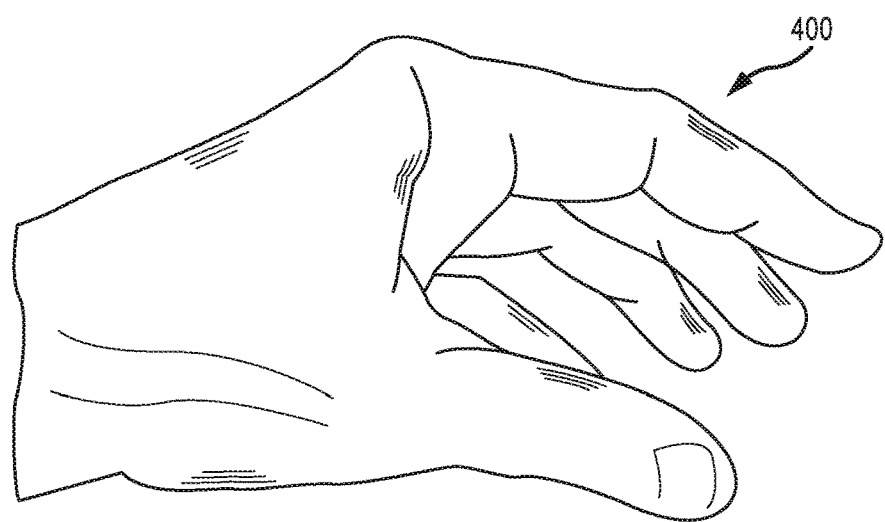
FIG. 3 depicts a hand in a suspended, normal relaxed position and not resting on a surface.

Turning now to the drawings where the purpose is to describe exemplary embodiments of the invention and not to limit the same, FIG. 1 illustrates a top view, FIG. 2 illustrates a side view, and FIG. 12 illustrates a bottom or palm view of a hand 200 in a relatively flat position with a surgical glove 102 thereon. A shape of a conventional glove is further illustrated in FIGS. 13(*a*) and 13(*b*), which illustrate a palm view and a side view of the conventional glove.

Figure 20:
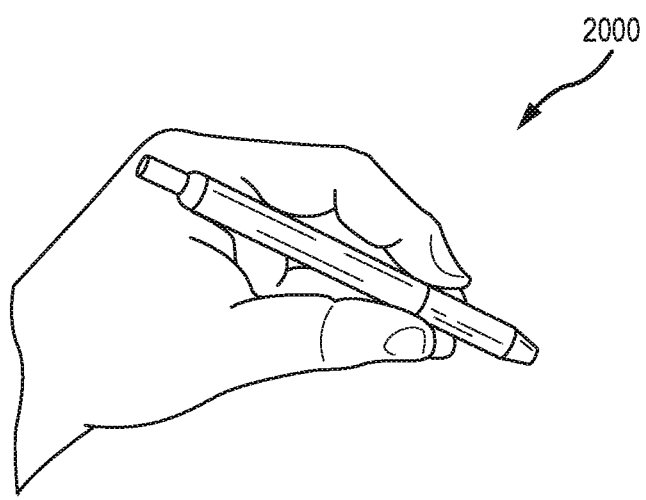
FIG. 20 illustrates a hand in a working position.

To facilitate understanding of the gloves described herein, various hand positions are illustrated in FIGS. 17-21. FIG. 17 illustrates a hand 1700 biased to flexion. FIG. 18A illustrates a side view of a hand 1800 in the straight position, which is the position in which standard gloves are formed. FIG. 18B illustrates a palm view of hand 1800. FIG. 19A illustrates a side, perspective view of a hand 1900 in a fully relaxed position and having cascading fingers. FIG. 19B illustrates a front view of the hand 1900. FIG. 20 illustrates a hand 2000 in a working position.

As is known, an MCP joint is a metacarpophalangeal joint. A PIP joint is a proximal interphalangeal joint. A DIP joint is a distal interphalangeal joint. An IP joint is an interphalangeal joint. And, a CMC joint is a carpometacarpal joint.

A thumb generally includes three joints. The most proximal thumb joint is the CMC joint between the trapezium and the thumb metacarpal. The thumb MCP joint is between the metacarpal and the proximal phalanx of the thumb. The distal most thumb joint is the IP or interphalangeal between the proximal and distal phalanges of the thumb.

Each finger, including the index, middle, ring and little fingers, has four joints including the CMC, MCP, PIP and DIP joints. The CMC joint of each finger is between the metacarpal and the carpal bone. The MCP joint of each finger is between the metacarpal and the proximal phalanx. The PIP joint of each finger is between the proximal and middle phalanges. The DIP joint of each finger is between the middle and distal phalanges.

Figure 4:
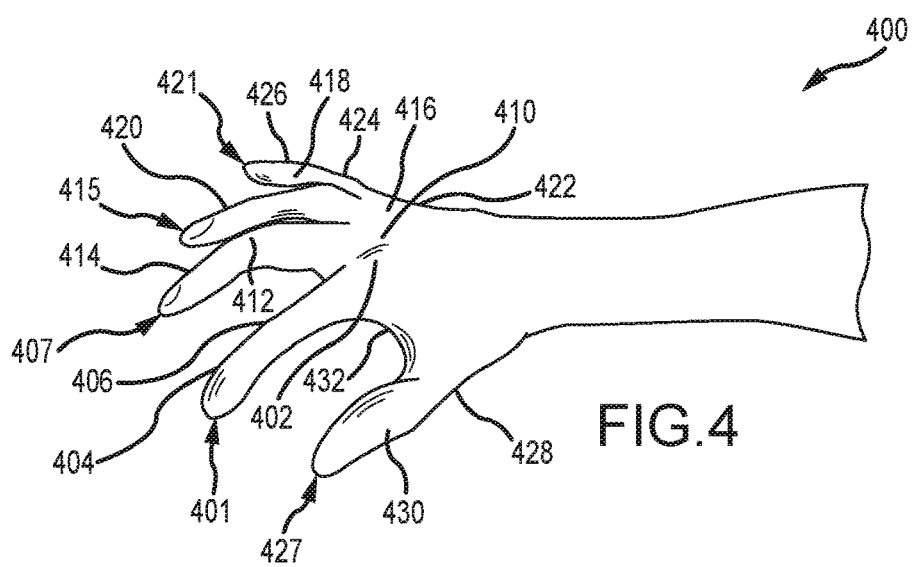
FIG. 4 illustrates a hand in a normal, relaxed position.
Figure 5:
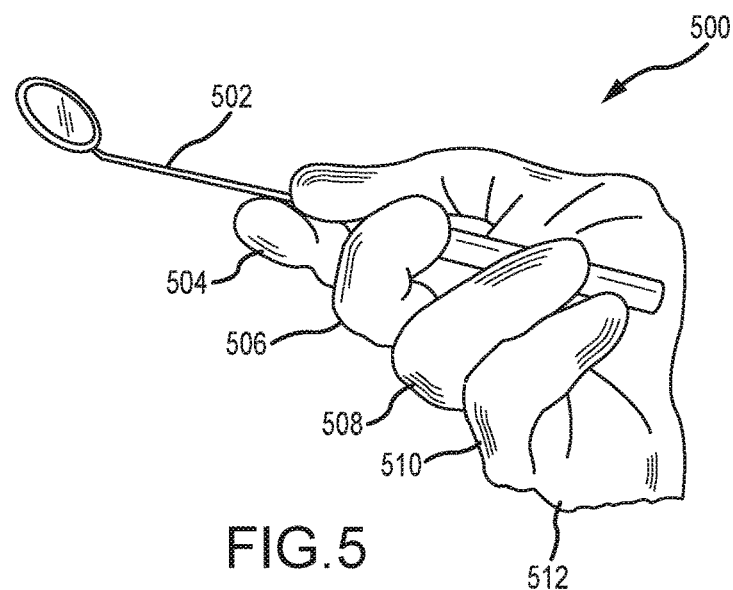
FIG. 5 depicts a hand with a conventional glove thereon, wherein the hand is grasping a dental instrument.

Turning to FIG. 4, respective portions of a hand 400 are shown. Index finger 401 has MCP joint 402, DIP joint 404, and PIP joint 406. Middle finger 407 has MCP joint 410, PIP joint 412, and DIP joint 414. Ring finger 415 has MCP joint 416, PIP joint 418 and DIP joint 420. Little finger 421 has MCP joint 422, PIP joint 424 and DIP joint 426. Thumb 427 has MCP joint 428 and IP joint 430. There is a space 432 between the thumb 427 and index finger 401. Not readily visible are the CMC joints of the fingers and thumb.

Gloves as described herein can be formed of any suitable material, such as medical-grade natural rubber latex, synthetic rubber material, cloth, leather, spandex, vinyl, or two more of any of these materials. Plus, they may include insulating or protective materials more than one layer, portions for increased tactile sensation, and/or cladding adding to flexible portions that provides protection while still allowing the material to expand and contract. Exemplary synthetic rubber materials include polychloroprene (neoprene), polyisoprene, styrene butadiene, styrene ethylene butadiene. Other suitable materials include nitrile and vinyl (polyvinylchloride). The thickness of the glove material may be any suitable amount and can range between, as an example, 0.14 mm-0.3 mm, or 0.5 mm to ¼", and glove thicknesses are known in the art and selected based upon the application. Gloves come in different sizes, with typical sizes ranging from 5½ to 9, which is also known in the art.

Figure 14:
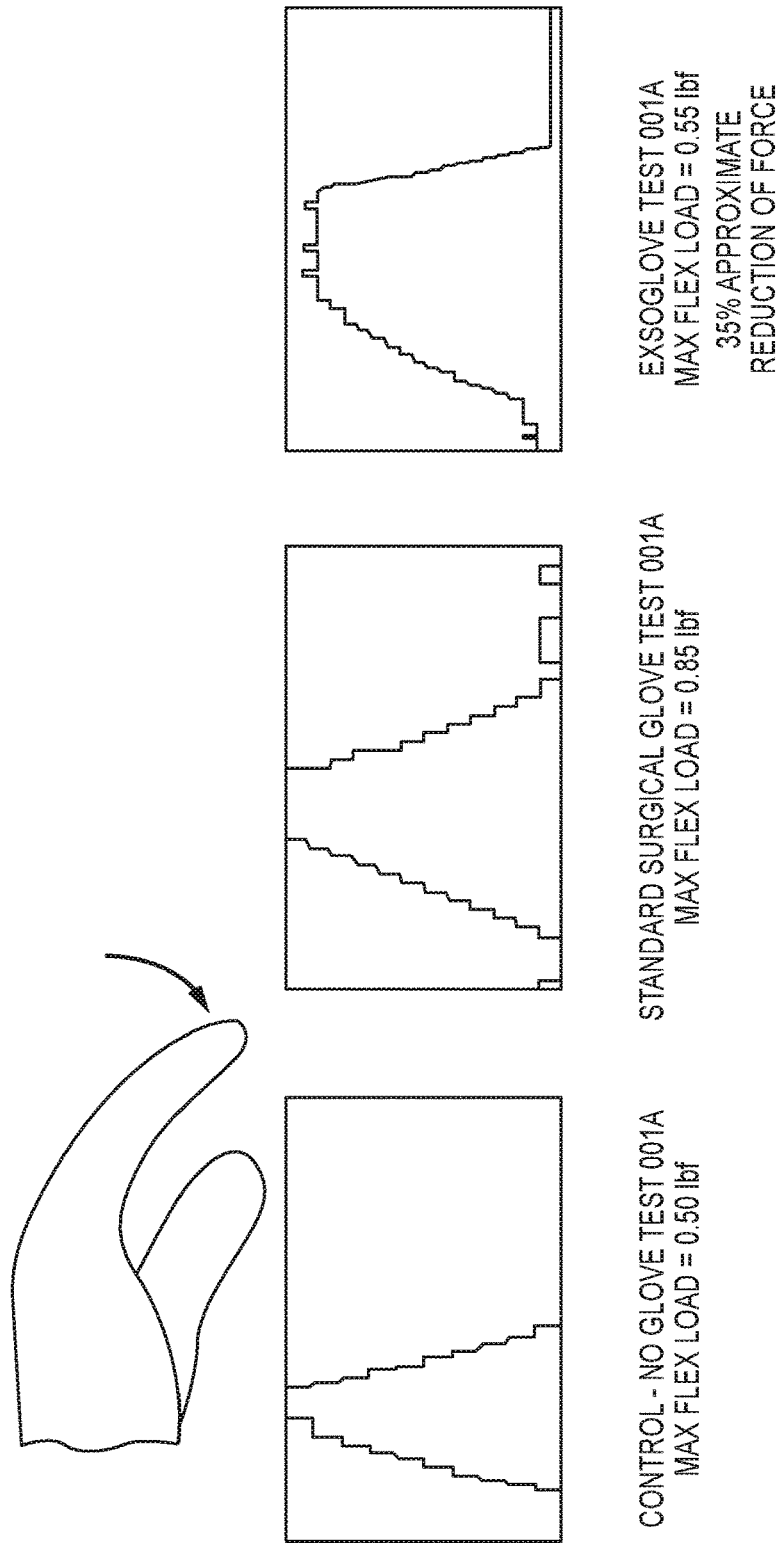
FIG. 14 illustrates comparative strain forces of fingers moving from the straight to the flexed position for various gloves.

Various embodiments of the glove designs described herein can be used alone or in any combination with the other designs and features noted herein. As noted herein, various advantages of the gloves herein described include a reduction of a biasing forces when the hand is opened and/or closed. FIG. 14 illustrates an exemplary reduction in flex load, compared to standard gloves. In this specific illustrated example, gloves in accordance with the present description reduced a flex load by about 35%, although the invention is not limited to this amount.

When referring to a location on a glove according to the invention, it may simply be referenced by the position on the hand (e.g., MCP joint of the index finger) or as a "location," "portion," or "position" or "location of the glove," "portion of the glove," or "position of the glove."

Flex Angles

Figure 21:
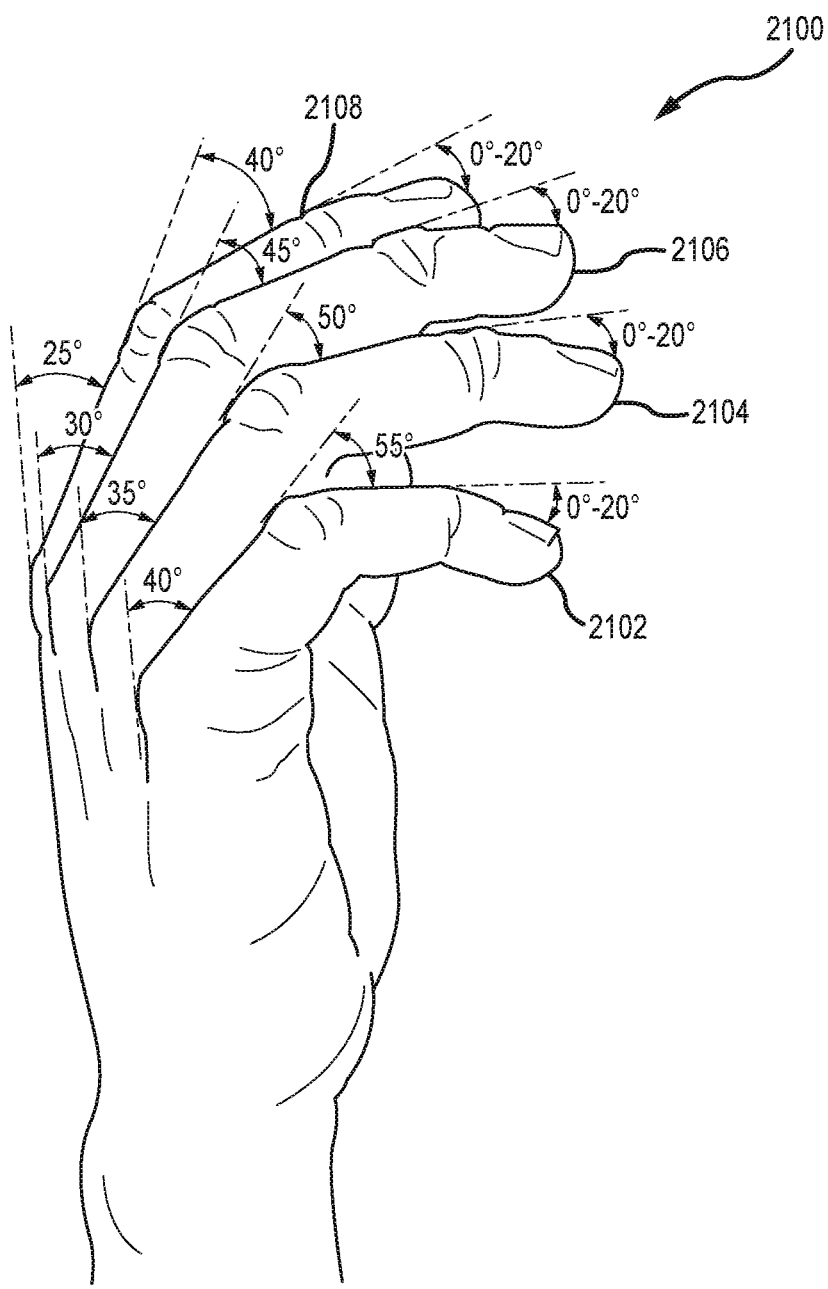
FIG. 21 illustrates a hand in a more natural position, but not the fully relaxed position, and shows the angles of the finger joints when in this position.

Exemplary gloves according to various embodiments of the invention are formed so the portions of the gloves corresponding to the fingers and/or thumb of a hand are more generally in a normal, relaxed hand position, but not entirely in the relaxed position, such as the position illustrated in FIG. 21. In this manner the hand can be closed and opened with limited resisting biasing forces on one or more of the digits and/or hand caused by the glove. By way of examples, portions of a glove corresponding to one or more of the MCP joints, one or more of the PIP joints and/or one or more of the DIP joints of a hand can be formed at a flex angle. A glove according to exemplary embodiments the invention preferably includes one or more of the following portions formed as follows: (a) the portion corresponding to the MCP joint of the index finger is formed at a flex angle of 10-45°, or 40°-50° (b) the portion corresponding to the MCP joint of the middle finger is formed at a flex angle of 10-45°, or 40°-50° (c) the portion corresponding to the MCP joint of the ring finger is formed at a flex angle of 15-50°, or 40°-50°, and (d) the portion corresponding to the MCP of the little finger formed at a flex angle of 20-55°, or 40°-50°.

Further, the following portions of the glove may be formed as follows: (a) the portion corresponding to the PIP joint of the index finger is formed at a 5-45°, or 10°-20°, flex angle, (b) the portion corresponding to the PIP joint of the middle finger is formed at a 5-50° or 10°-20°, flex angle, (c) the portion corresponding to the PIP joint of the ring finger is formed at a 10-55° or 10°-20°, flex angle, and (d) the portion corresponding to the PIP joint of the little finger is formed at a 15-60°, or 10°-20°, flex angle.

Also, (a) the DIP joint of the index finger may be formed at a 5°-25°, or 10°-20°, or 0°-20°, flex angle, (b) the DIP joint of the middle finger may be formed at a 5°-25°, or 10°-20°, or 0°-20°, flex angle, (c) the DIP joint of the ring finger may be formed at a 10°-30°, or 10°-20°, or 0°-20°, flex angle, and (d) the DIP joint of the little finger is formed at a 15°-30°, or 10°-20°, or 0°-20°, flex angle.

Additionally or alternatively, one or more of the following portions of a glove corresponding to the thumb may be formed as follows: (a) the portion corresponding to the MCP joint of the thumb is formed at a flexed angle of 10-45°, and (b) the portion corresponding to the IP joint of the thumb is formed at a flexed angle of 20-50°.

Additionally, gloves according to various exemplary embodiments of the invention can include a two-radius curve, meaning that the angles of the MCP joints are flexed at a greater angle than the other joints.

In one embodiment, the portions of the glove corresponding to the MCP joints have greater flex angles than either the PIP and DIP joints, such that the fingers in the hand remain open to some degree, rather than being in their fully relaxed position. One embodiment of preferred flex angles are approximately:

|           | Index finger | Middle finger | Ring finger | Little finger |
|-----------|--------------|---------------|-------------|---------------|
| MCP joint | 25°          | 25°           | 30°         | 35°           |
| PIP joint | 15°          | 15°           | 20°         | 25°           |
| DIP joint | 15°          | 15°           | 20°         | 25°           |

Although these angles are less than the complete relaxed position of the hand, they allow for: ease of manufacturing, helping to keep the hand open to some degree, and preventing too much bias against opening or closing the hand.

Any of the flex angles set forth herein could possibly be varied beyond the stated ranges to better approximate the shape of a hand in a position to reduce biasing forces when the hand opens or closes.

Figure 30A:
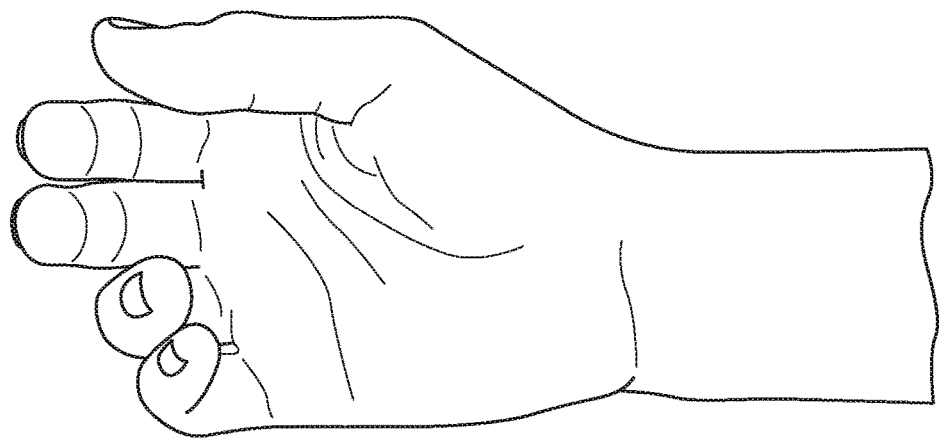
FIGS. 30A and 30B depict a hand in its normal cascade position in which the joints and muscles are in a resting position.
Figure 30B:
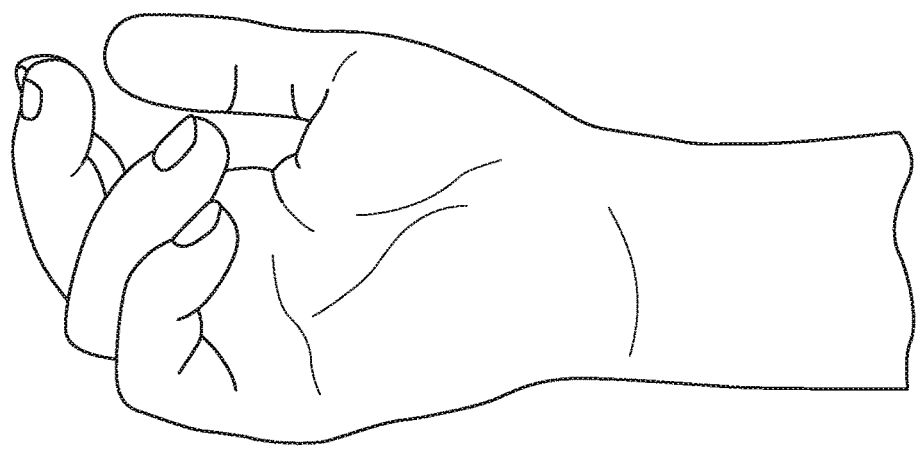
Figure 31:
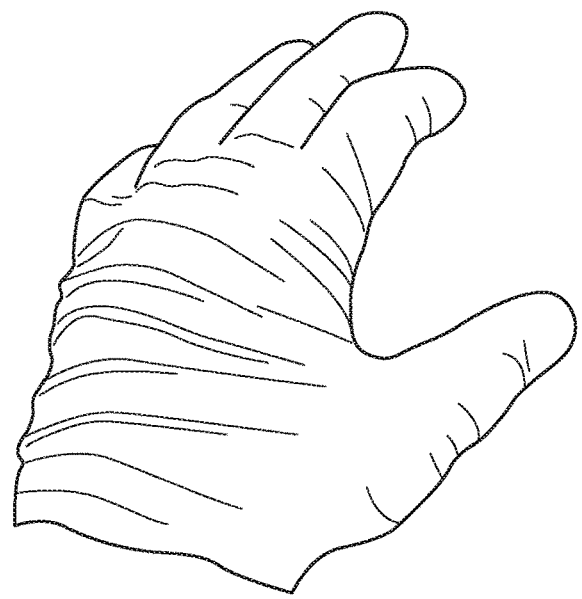
FIG. 31 depicts an oversized glove on a hand.
Figure 32:
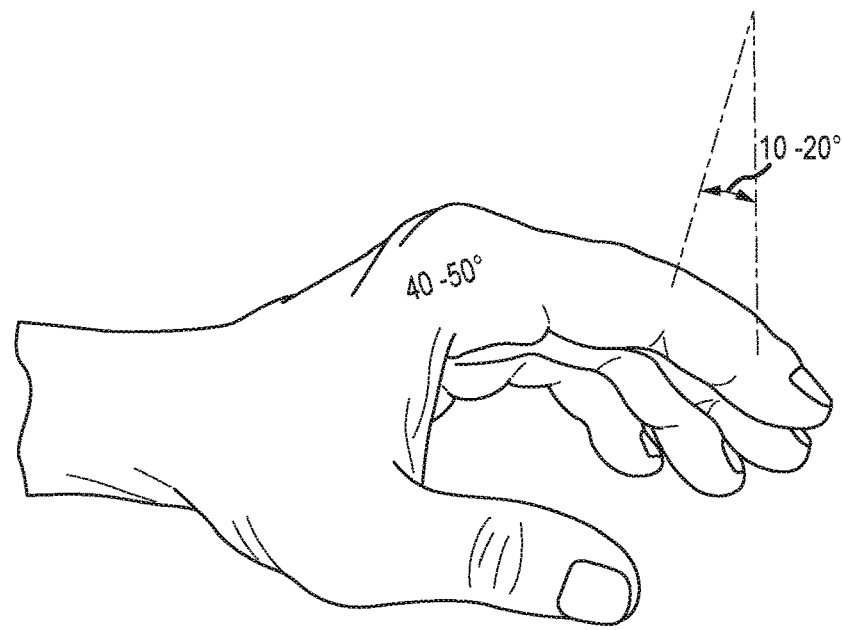
FIG. 32 depicts a hand open slightly from its normal cascade position.
Figure 33:
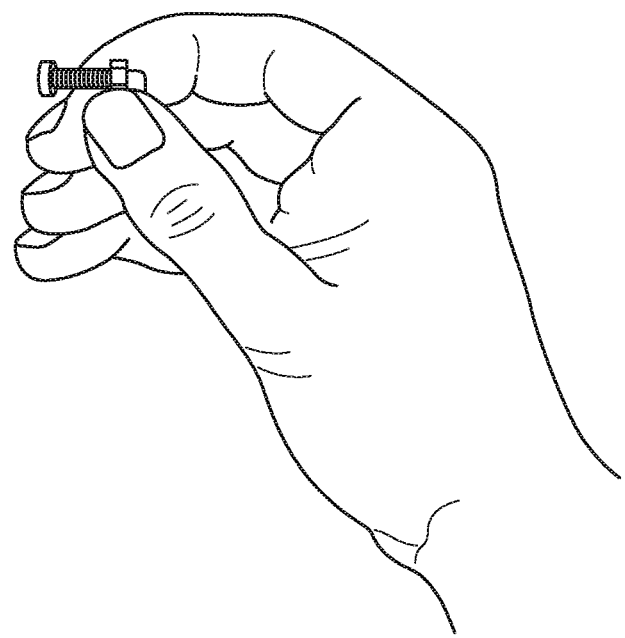
FIG. 33 depicts a hand wherein the thumb, index finger and middle finger are pressed together to grasp a small object.
Figure 34:
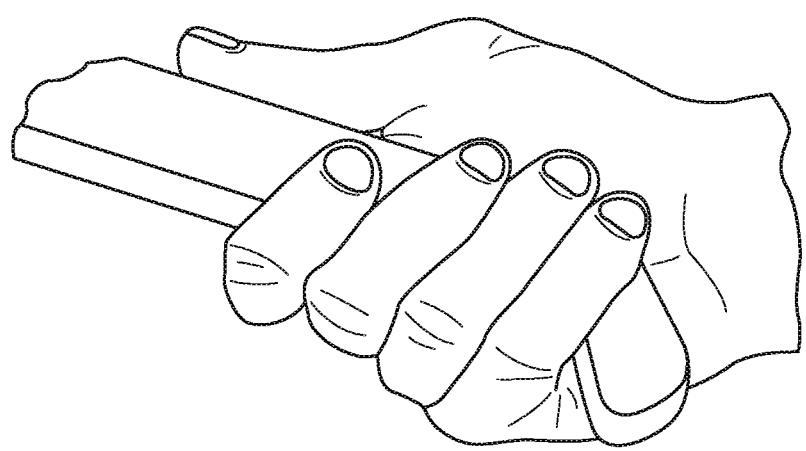
FIG. 34 depicts a hand clenched around an object using the three ulnar digits and thumb.
Figure 35:
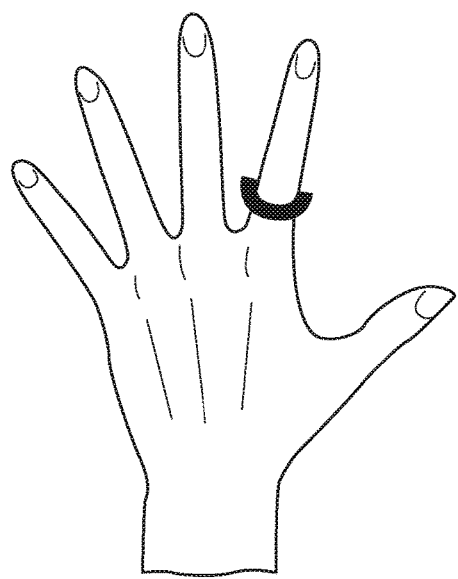
FIGS. 35-37 depict the increase in digit circumference when digits go from the fully extended to the closed position.
Figure 36:
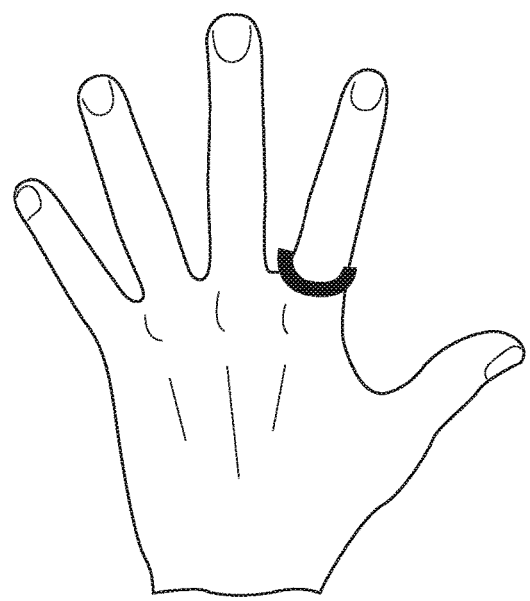
Figure 37:
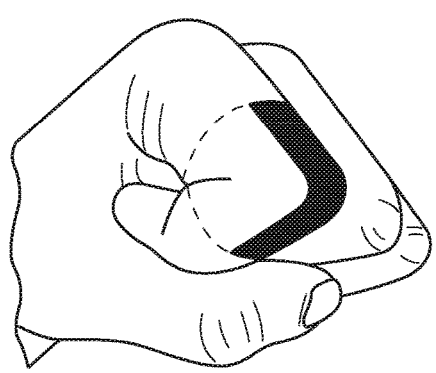
Figure 38A:
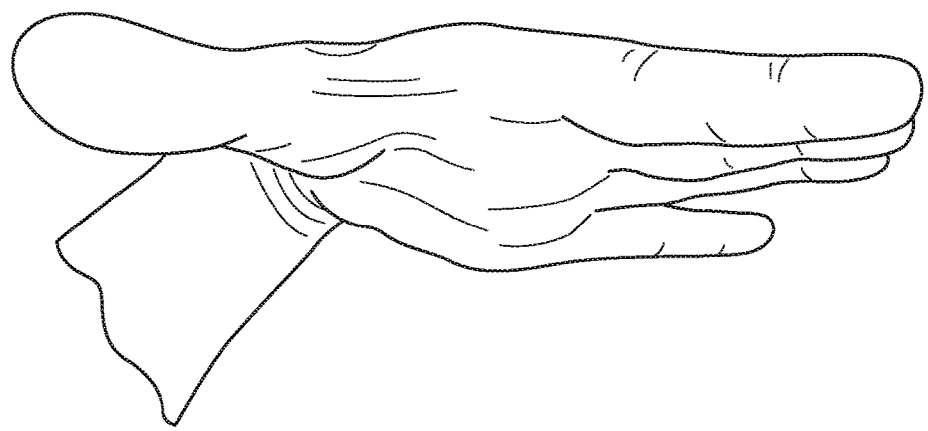
FIG. 38A depicts a hand showing the region in the space between the thumb and index finger when the thumb is moved away from the index finger a maximum amount.
Figure 38B:
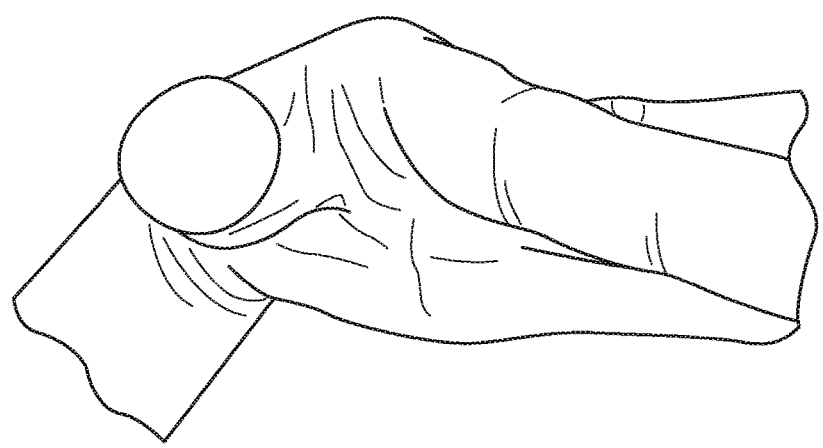
FIG. 38B depicts the hand of FIG. 38A wherein the thumb is partially closed against the index finger.
Figure 38C:
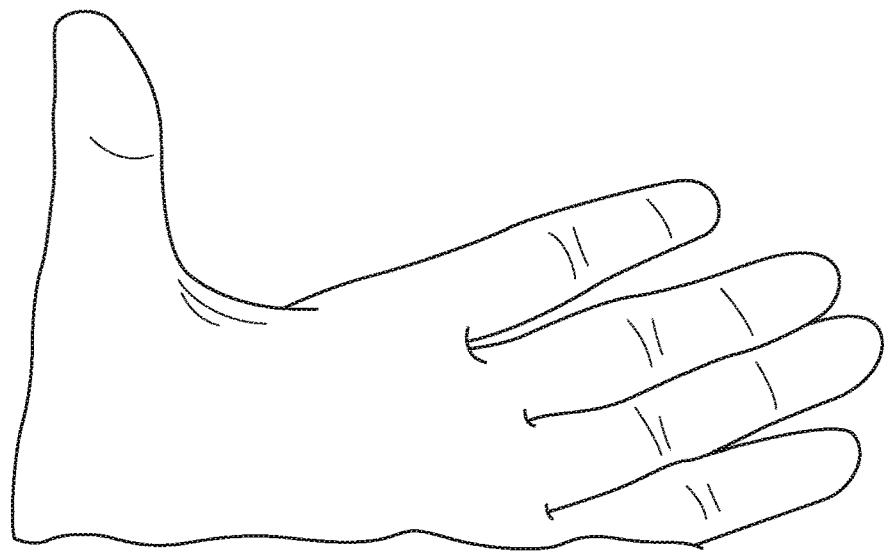
FIG. 38C depicts a palm view of the hand of FIG. 38A.
Figure 38D:
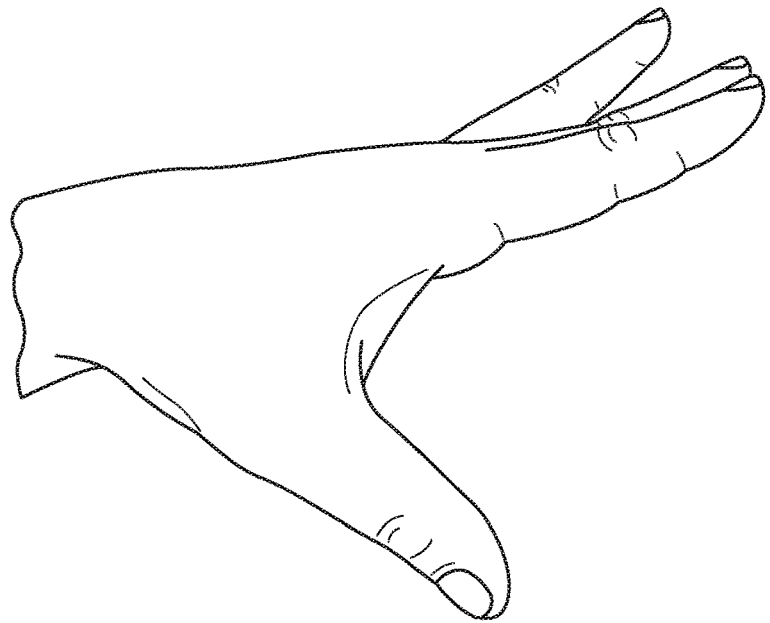
FIG. 38D depicts a side view of the hand of FIG. 38A and FIG. 38C.
Figure 38E:
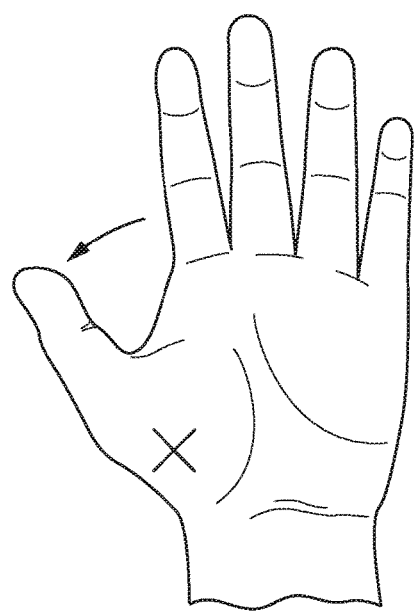
FIG. 38E depicts the palm view of a hand with the digits extended illustrating how the thumb can move away from the index finger.
Figure 38F:
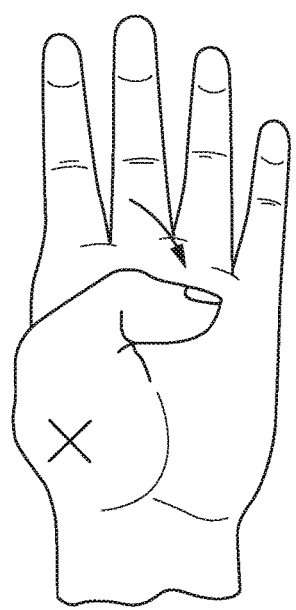
FIG. 38F depicts the hand of FIG. 38E and shows how the thumb can move in a different plane towards the palm to oppose the palm or fingers.
Figure 38G:
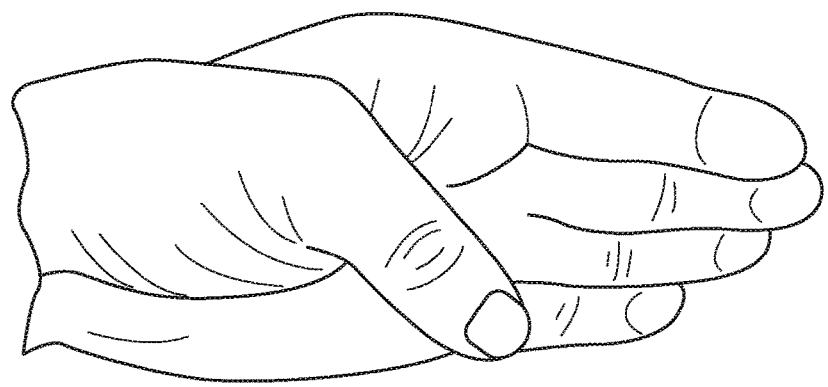
FIG. 38G is a side view of a hand with the thumb in a closed position.
Figure 38H:
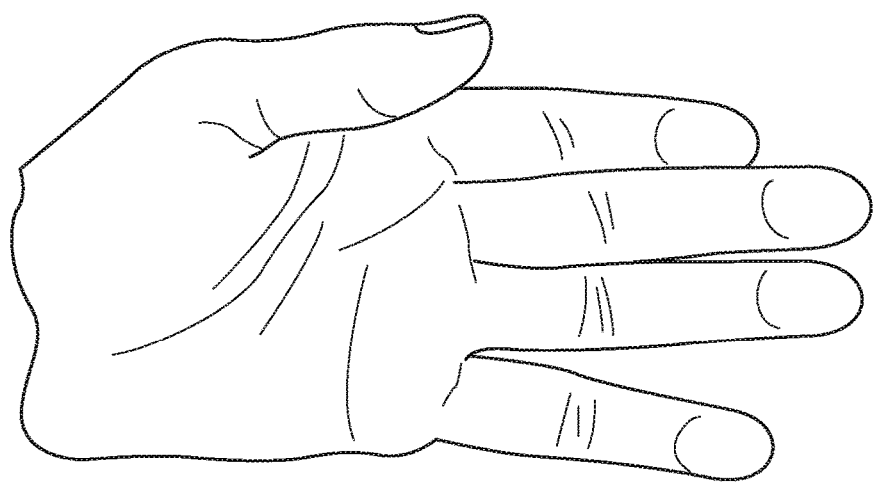
FIG. 38H is a side view of a hand with the thumb partially closed and resting against the index finger.
Figure 39:
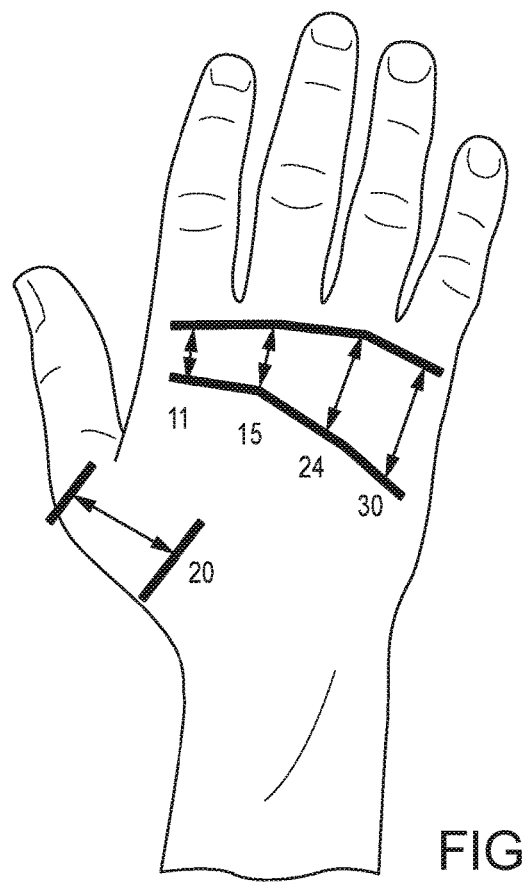
FIG. 39 depicts the approximate amount of extra material (if all of the extra material is provided at the MCP joint of each finger and the PIP joint of the thumb) to be added to a glove to compensate for the amount the top of each digit extends when it moves from the extended to the closed position.
Figure 40:
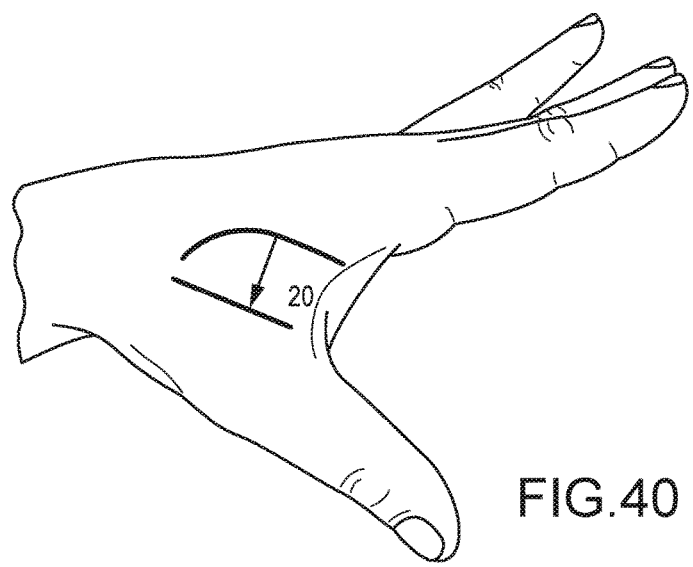
FIG. 40 depicts a typical hand with the thumb fully extended from the index finger and shows the approximate amount the skin in the region depicted expands.
Figure 41:
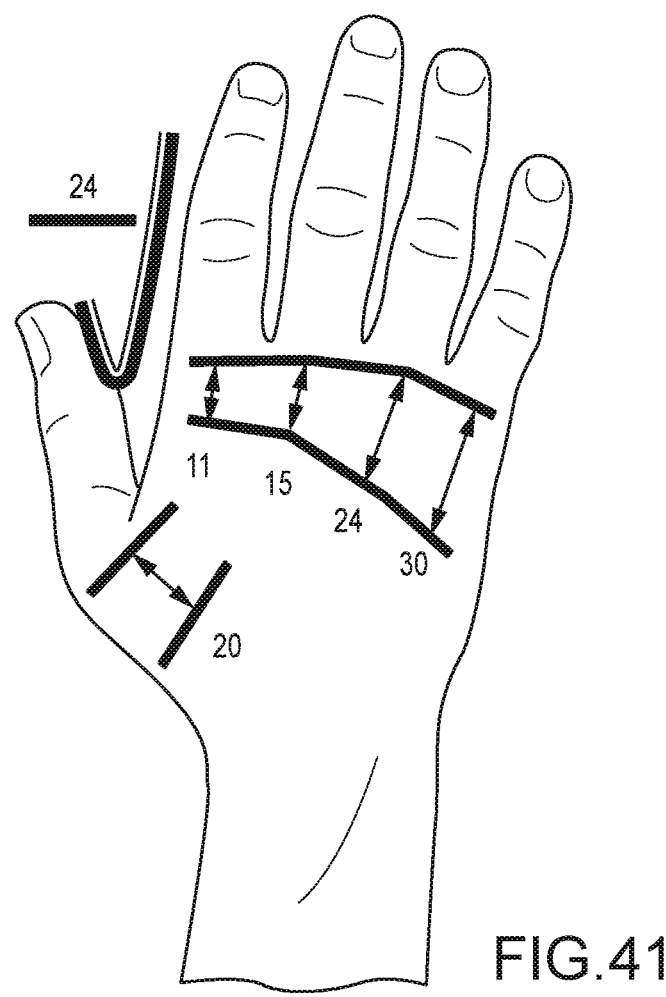
FIG. 41 depicts a hand and shows the approximate amount of expansion that occurs along regions of the digits when they move from the extended to the closed position.

Another aspect of the invention is that when in a relaxed position, the fingers may be in a cascading position moving from the index finger to the little finger, with the flex angles of the joints of each finger varying. An example of a hand 2100 including cascading fingers 2102-2108 is illustrated in FIG. 21. FIGS. 30A and 30B depict a hand in its normal cascade position in which the joints and muscles are in a resting position. FIG. 32 depicts a hand open slightly from its normal cascade position. Some embodiments of the gloves disclosed herein include one of these cascading features, and most preferably are not in the fully relaxed, cascading position, but are about 5°-10° more extended.

One way in which a glove according to the invention compensates for this cascading position is by providing different flex angles, or features to permit flexing, at the various joints. Exemplary angles for the cascading digits are illustrated in FIG. 21, and these angles may fall within ranges as set forth in the exemplary embodiments herein.

Additionally, the palm region of the glove may be formed at a suitable flex angle, such as between 10°-30°. Moreover, a glove according to the invention may have the thumb portion formed in a more natural position with the thumb in a different plane than the fingers.

Figure 25A:
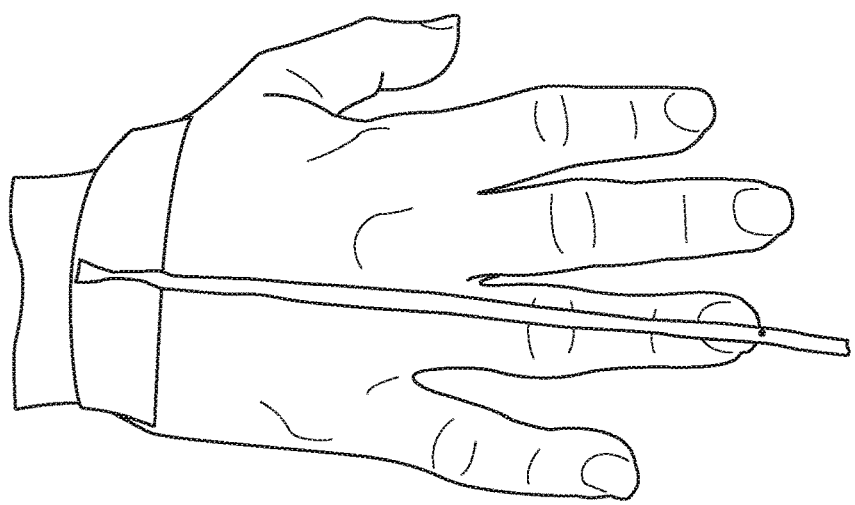
FIG. 25A illustrates the hand in a flat position with the figures extended.
Figure 25B:
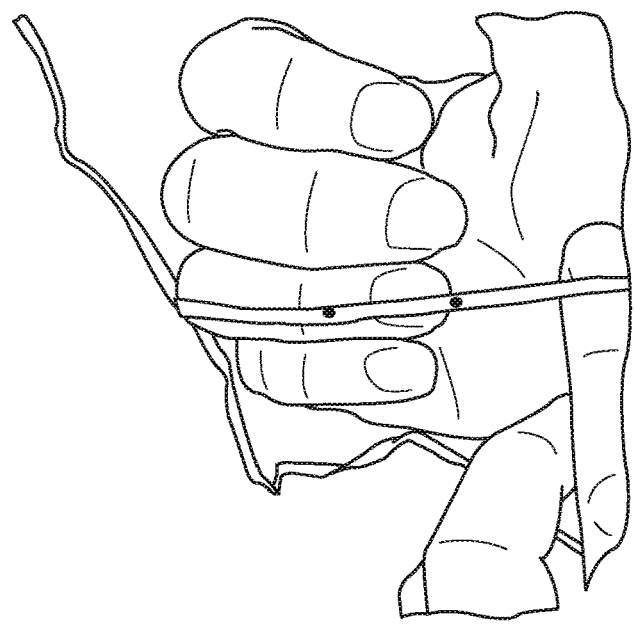
FIG. 25B illustrates the hand of FIG. 25A with the fingers flexed to essentially a fully-closed position.

When the fingers are flexed from an extend to a closed position, as illustrated in FIGS. 25A-25B, the length along the top of the finger, measured from a position just behind the MCP joint of the finger increases. For a size 6.5 glove and 8.0 glove, the length along the top of each finger increases by approximately the amounts shown below:

|                | Index finger | Middle finger | Ring finger | Little finger |
|----------------|--------------|---------------|-------------|---------------|
| Size 6.5 glove | 10 mm        | 13 mm         | 20 mm       | 32 mm         |
| Size 8.0 glove | 11 mm        | 15 mm         | 24 mm       | 30 mm         |

The difference in increased length moving from the index finger to the little finger is because of the cascading shape of the hand when relaxed or closed.

Figure 26:
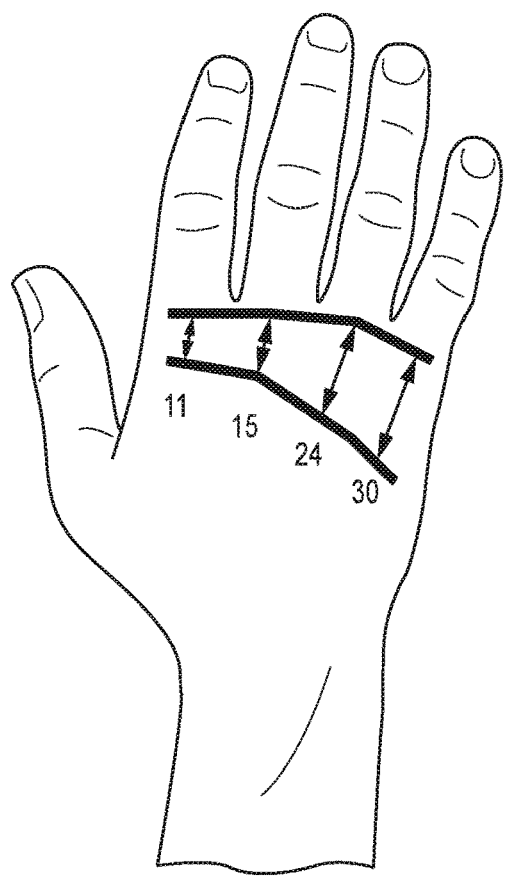
FIG. 26 is a top view of a hand illustrating the amount of extra material or stretch (as measured from the MCP joints) for the fingers to move from a straight to a cascading position for a size 8 glove.
Figure 27:
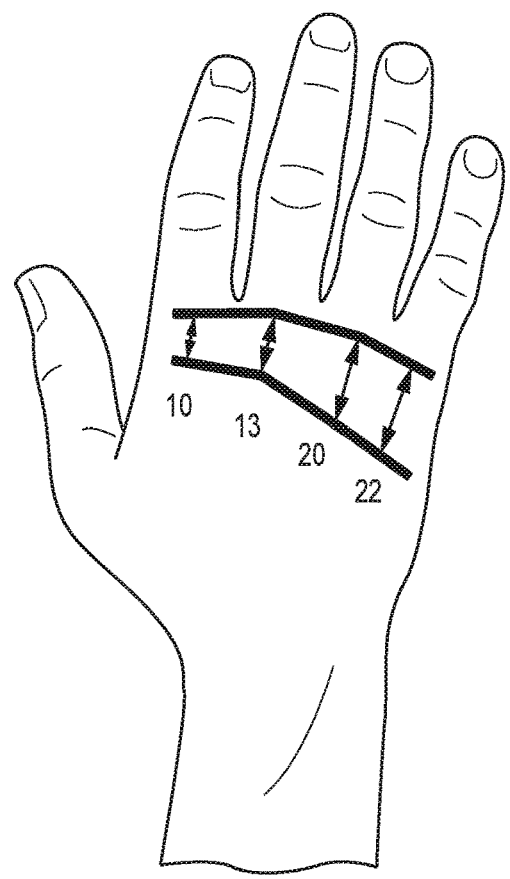
FIG. 27 illustrates the amount of extra material or stretch (as measured from the MCP joints) for the fingers to move from a straight to a cascading position for a size 6.5 glove.

Therefore, it is desirable to provide extra material for the tops of the fingers (and thumb) when in the closed position to reduce biasing forces. This can be done by pre-flexing the glove as described herein so it is formed in a position that is close to, but preferably not quite, in the position of a relaxed hand and/or by including patterns. In one embodiment corresponding to the above chart, all of the extra material is provided at the MCP joint of each finger, as illustrated in FIG. 26 (for a size 8.0 glove) and 27 (for a size 6.5 glove). The extra material is preferably (a) half provided by the flex angles for the MCP joints disclosed herein, and (b) half provided by patterns (discussed below). Alternatively, the extra material may be entirely provided by flex angles at two or more joints of a finger, or by flex angles at two or more joints of each finger and patterns at one or more joints of each finger.

Figure 28C:
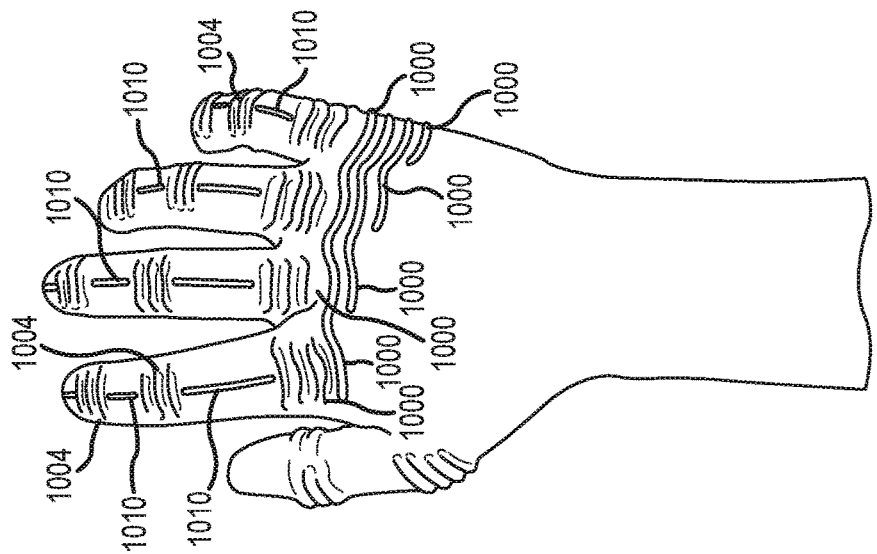
FIG. 28C is a top view of the glove of FIG. 28A.
Figure 28B:
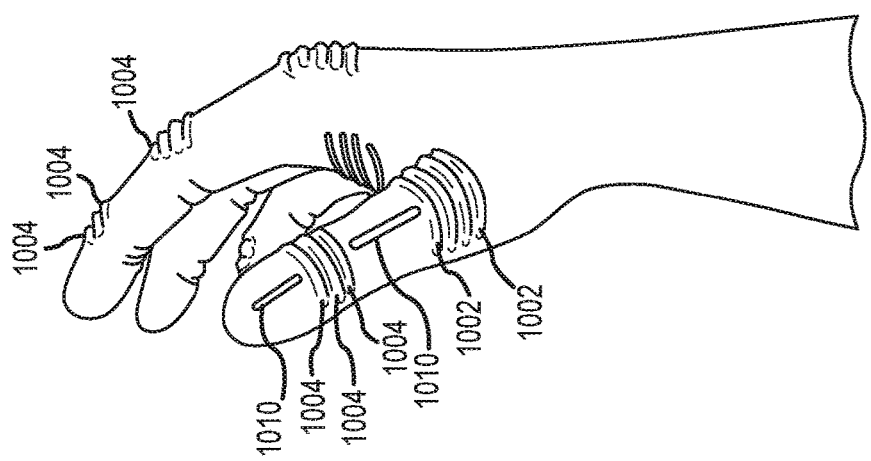
FIG. 28B is a side view of the glove of FIG. 28A.
Figure 28A:
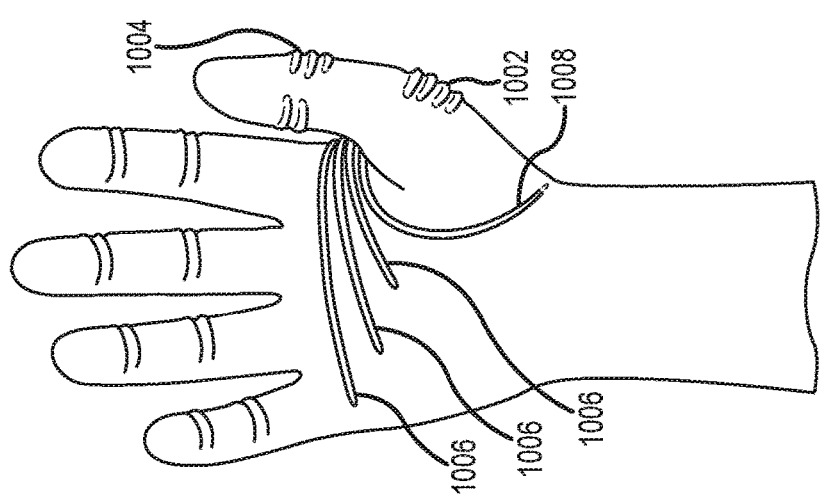
FIG. 28A is a palm view of a glove in accordance with an embodiment of the invention.
Figure 29:
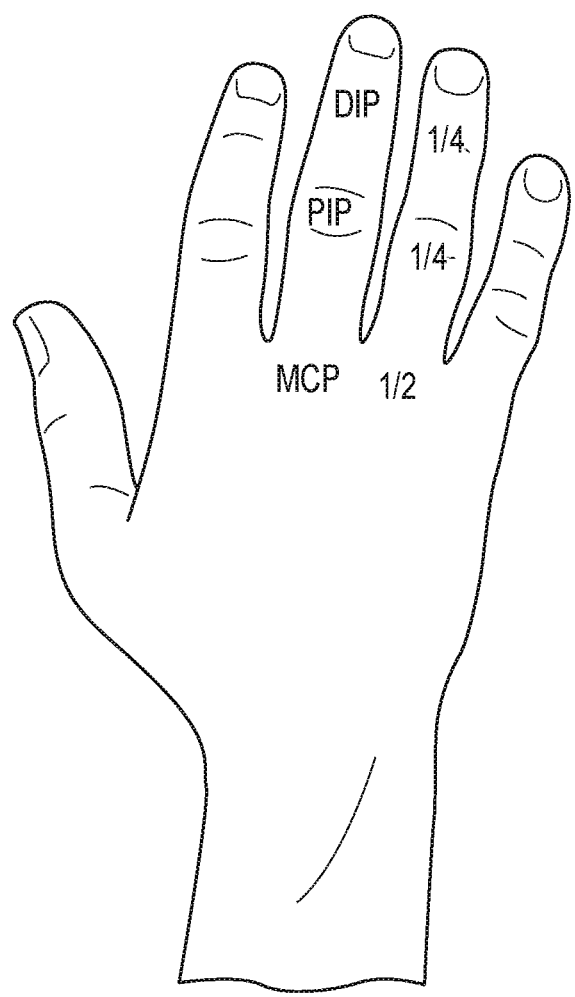
FIG. 29 is a top view of a hand.

FIGS. 28A-28C show a glove in accordance with the invention wherein approximately ½ of the extra material required along the top side of the finger when fully flexed is provided by flex angles at each finger joint and about half is provided by patterns, which are preferably ribs at each joint. As shown in FIG. 29, in one embodiment, about ½ of the extra length required for fully closing each finger is provided at the MCP joint, about ¼ is provided at the PIP joint and about ¼ is provided at the DIP joint.

Patterns

Figure 6:
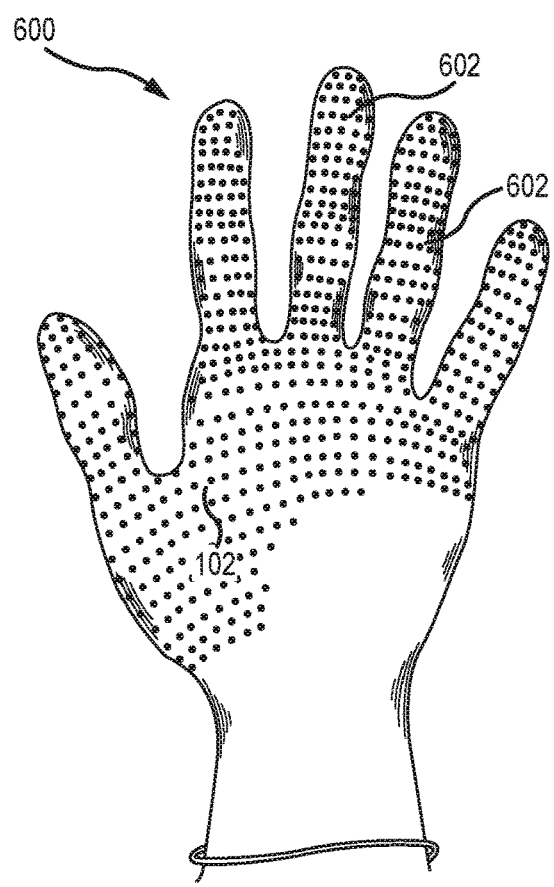
FIG. 6 depicts a top view (wherein the flexed angles of the joints cannot be readily seen) of an exemplary glove that includes a pattern.

A glove according to the exemplary embodiments of the invention can additionally or alternatively have a pattern formed therein at various positions that allows easier flexing of the glove material. Some exemplary patterns are shown in FIGS. 6-6E and each provides additional material for opening and/or closing the hand to reduce biasing forces when stretched, and reduce or eliminate a baggy fit when not stretched. The pattern may be one or more of the following:

(1) Any feature with about 10 mm or less of total height or depth that permits a glove to flex with less force when the hand is opened, closed or both.

(2) The material forming the glove may be ribbed, wherein the ribs (which are folds of material) include excess material to permit expansion of the glove and the ribs may extend about ⅛" or less beyond the outer surface of the glove on either the dorsum side, palm side, between the fingers, between the thumb and fingers, or some combination thereof. FIG. 2 illustrates a dorsum D side of hand 200 and a palm side P of hand 200.

(3) The material forming the glove can have a pattern of (e.g., alternating) raised portions and/or depressions, wherein the center of each raised portion or depression is preferably no greater than 1/4" inches apart from other portions, and most preferably no greater than 1/8" to 1/32" apart. The raised or depressed portions are preferably formed in one or more of cross-sectional shapes from the group consisting of: semi-oval, semi-circle, square, rectangular, triangular, three-sided pyramidal and four-sided pyramidal. The pattern may follow the natural contour of the hand where desired. This can create nonlinear and asymmetrical patterns.

A glove can include a more concentrated pattern of patterns proximate areas corresponding to areas of the digits and hand that bend or stretch, thereby allowing easier bending at the areas that need to bend more, such as at one or more of the MCP, PIP, DIP, or IP joints, or in area 32 between the thumb and index finger, or in the web spaces between the other fingers. As another example, a pattern may be present and/or more concentrated along the axis of the dorsum of the little finger, or be more concentrated from the mid hand to the mid proximal phalanx. Or, the pattern may cover any portion of the dorsum or palm. On the index finger, the pattern may cover the distal hand to the proximal phalanx. The pattern may be biased toward the ulnar side of the hand where biasing forces are greatest. On the thumb MCP joint, the pattern may predominate on the dorsum, but might extend into area 32. Additionally, the pattern may be placed along the longitudinal axis of one or more of the fingers and/or thumb.

A glove including a pattern might include the same pattern or different patterns, such as one pattern at one or more of the joints, and another between the spaces between the fingers. For example, alternating raised portions or depressions in the form of a four-sided pyramid may be at any suitable location on the gloves, including on part of or the entire palm side of the glove, and there may be ribs running into the spaces between the fingers, or on the flexor surface of the gloves to relieve biasing forces of extending fingers associated with pre-relaxed gloves. The ribs allow easier expansion to decrease the loads on the digits with abduction of the fingers or wide stretching of the hand, in the same fashion as one would need to play far apart piano keys. The glove can include a pattern over or under any of the joints of one or more of the digits. Further, a pattern can be placed in the mid palm to provide some relaxation during maximal extension of the fingers.

Other Exemplary Embodiments

As shown in FIGS. 28A-28C, a glove according to the invention has patterns formed as ribs. In this embodiment ribs 1000 are positioned at the top of each MCP joint and either encircle, or are on the top and palm side, of each PIP joint and DIP joint. The ribs also encircle the thumb PIP and IP joint, and extend along the palm and into the space between the thumb and index finger. There are four separate, non-connected ribs positioned at the thumb PIP joint; four separate, non-connected ribs positioned at the index finger MCP joint, five separate, non-connected ribs at the MCP joint of the middle finger; six separate, non-connected ribs at the MCP joint of the ring finger; and seven separate, non-connected ribs at the MCP joint of the little finger.

In this embodiment, one rib 1000, which is the fourth rib (as measured from the distal ends of the fingers) for each of the index finger, middle finger, ring finger and little finger, is continuous to assist in flexion of the hand between the fingers. Another rib 1000, which is the fifth rib (as measured form the distal ends of the fingers) for each of the middle finger, ring finger and little finger, is continuous to assist in flexing of the hand. Another rib 1000 is the sixth rib (as measured from the distal ends of the fingers) for each of the ring finger and little finger and assists in flexing of the hand. The IP joint of the thumb has four separate, non-connected ribs 1002, and the PIP and DIP joint of each finger has three separate, non-connected ribs 1004.

The ribs in this example have a curved relief at the MCP joints, wherein the end of each rib at an MCP joint is preferably between 1 mm to 3 mm closer to the distal end of the respective finger on which it is positioned than the center of the rib.

There are also three separate, non-connected ribs 1006 in the palm section, wherein the uppermost rib extends under the little finger, the center rib extends to approximately a position between the little finger and ring finger, and the lower rib extends to approximately the ring finger. There is also an additional rib 1008 running along the muscle of the thumb to assist in flexing the thumb towards the palm or fingers.

Additionally, this example has ribs 1010 extending longitudinally between the MCP joint and PIP joint of each finger, the PIP joint and DIP joint of each finger, the PIP joint and the IP joint of the thumb, and distal of the IP joint of the thumb. Each of these ribs can expand by 1 mm to 10 mm.

Patterns according to the invention may provide between 1 mm to 250 mm of extra material depending upon their location on the glove. For example, a pattern positioned at the MCP joint of the: (a) index finger may provide 2 mm to 15 mm, or 2 mm to 11 mm of extra material, (b) the middle finger may provide 3 mm to 20 mm, or 3 mm to 15 mm, of extra material, (c) the ring finger may include 4 mm to 25 mm, or 4 mm to 24 mm, or extra material, and (d) the little finger may include 5 mm to 30 mm, or 5 mm to 35 mm, of extra material. A pattern positioned at the PIP and/or DIP joint of the: (a) index finger may provide 1 mm to 8 mm, or 1 mm to 10 mm, of extra material, (b) middle finger may provide 1 mm to 11 mm, or 2 mm to 10 mm, of extra material, and (c) ring finger may include 2 mm to 13 mm, or 2 mm to 10 mm, or extra material. A pattern positioned at the thumb PIP joint may provide for 5 mm to 20 mm of extra material, and a pattern positioned at the thumb IP joint may provide for 8 mm to 20 mm of extra material.

A pattern positioned between the thumb and index finger may provide 20 mm to 250 mm of extra material and pattern positioned between any two fingers may provide 20 mm to 200 mm of extra material. A pattern on the palm may provide 30 mm to 350 mm of extra material.

Some non-limiting examples of gloves having different patterns are illustrated in FIGS. 6-11. FIG. 6 illustrates a glove 600 having a pattern 602. As illustrated, pattern 602 covers all of the joints of the digits, the space between the thumb and index finger, and the spaces between each finger. Pattern 602, or any suitable pattern used with the gloves described herein, could cover any suitable portion of the glove, such as one or more of: the portion corresponding to one or more joints, the portion corresponding to the space between the thumb and index finger, any or all spaces between the fingers, the dorsum, and the palm.

FIGS. 6A-6E illustrate close up, side views of exemplary structures suitable for pattern 602. FIG. 6A illustrates pattern 602(a) as raised square or rectangular sections. FIG. 6B illustrates pattern 602(b) as raised triangular sections, which would be pyramidal if viewed in three dimensions. FIG. 6C illustrates pattern 602(2) as raised flat-topped pyramidal sections. FIG. 6D illustrates pattern 602(d) as raised broad partial ovoid or partial spherical sections. FIG. 6E illustrates pattern 602(e) as raised dome-like sections. Any suitable structures, or combination of structures, however, could be used to form pattern 602.

FIG. 7 illustrates a glove 700 according to various embodiments of the invention with ribs 702 to assist with easier flexing. Exemplary ribs 702 are formed in the material of glove 700 and are preferably no higher than about 2 mm, although any suitable height can be used. The spacing between the ribs may be any suitable spacing and may vary at different areas of the glove. Preferably, the ribs 702 are spaced apart between 1/16" and 1/4."

Figure 8:
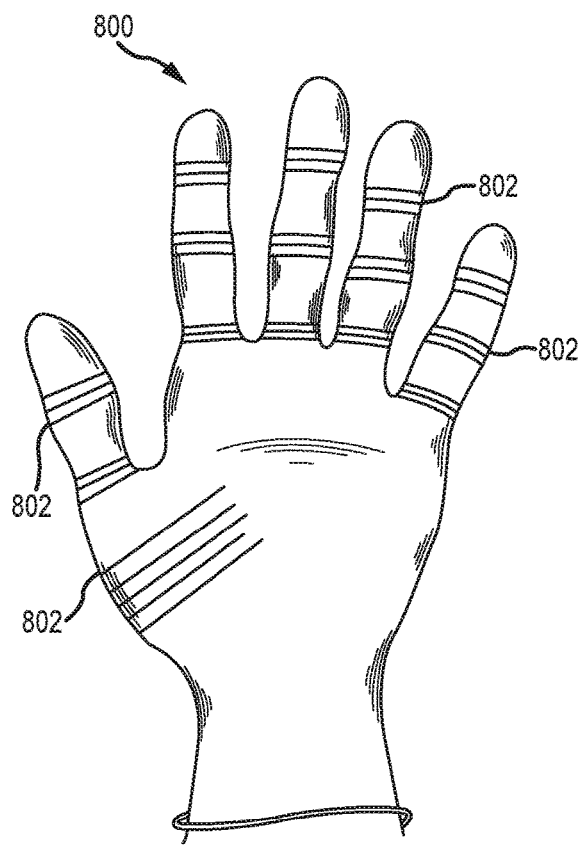
FIG. 8 depicts a top view (wherein the flex angles of the joints cannot be readily seen) of an exemplary glove that includes a pattern of ribs in selected portions of the glove.

FIG. 8 illustrates a glove 800 according to further exemplary embodiments of the invention with ribs 802 to assist with easier flexing. Exemplary ribs 802 can be the same as previously described ribs 702, except ribs 802 only extend along the portions of the glove that correspond to the locations of the joints.

Figure 9:
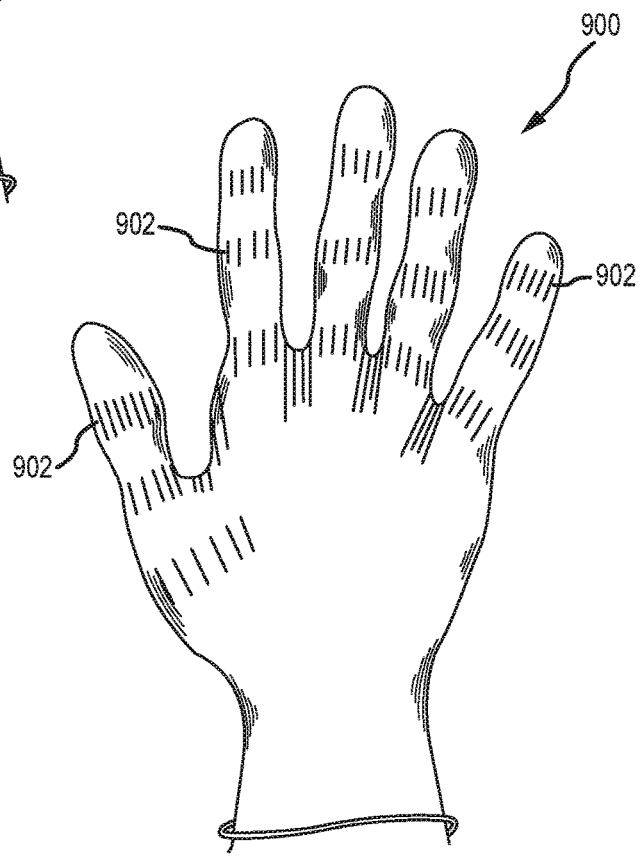
FIG. 9 depicts a top view (wherein the flex angles of the joints cannot be readily seen) of an exemplary glove that includes a pattern of ribs in selected portions of the glove, wherein the ribs are axially oriented to the digits.

FIG. 9 illustrates a glove 900 according to yet further exemplary embodiments of the invention with ribs 902 to assist with easier flexing. Exemplary ribs 902 are formed in the material of glove 900, are axially-aligned along the digits, and are preferably no higher than 2 mm, although any suitable height can be used. The spacing between the ribs may be any suitable spacing and may vary at different areas of the glove. Preferably, the ribs 902 are spaced apart between 1/16" and 1/4."

Figure 10:
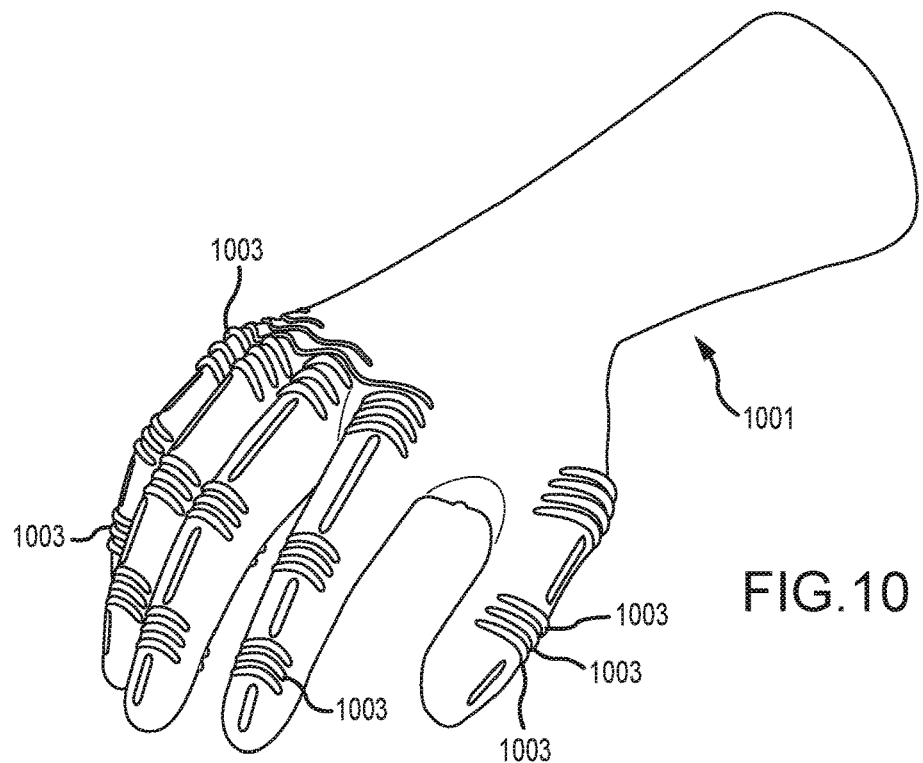
FIG. 10 depicts a top, perspective view of an exemplary glove that includes a pattern of ribs in selected portions of the glove.

FIG. 10 illustrates a glove 1000 according to additional exemplary embodiments of the invention with ribs 1002 to assist with easier flexing. Ribs 1002 are formed in the material of glove 1000 and are preferably no higher than 2 mm, although any suitable height can be used. The spacing between the ribs 1002 may be any suitable spacing and may vary at different areas of the glove. Preferably, the ribs 1002 are spaced apart between 1/16" and 1/4."

Figure 11:
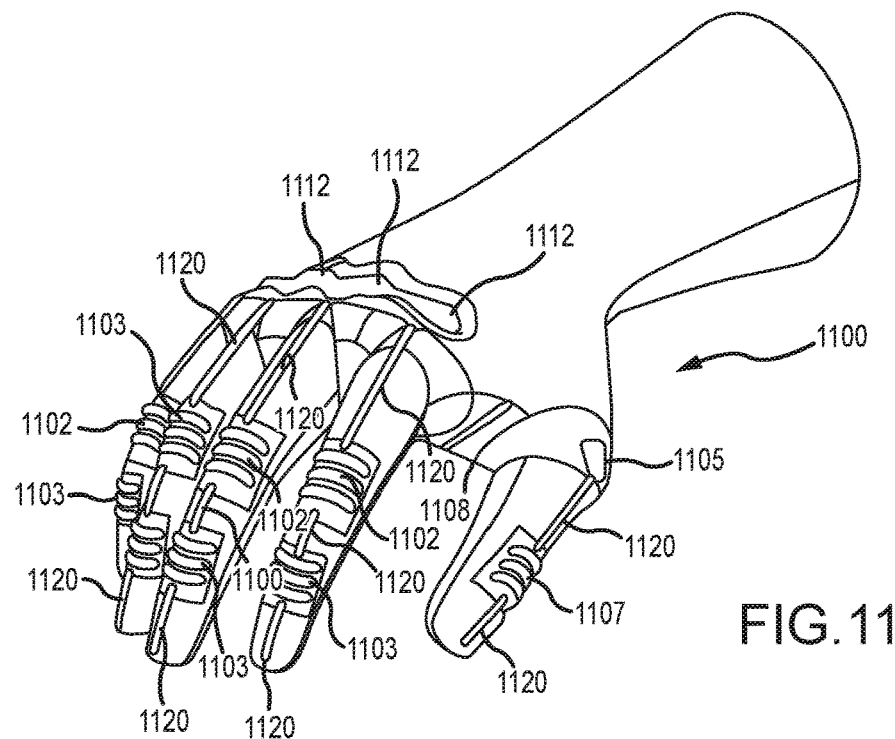
FIG. 11 depicts a top, perspective view of a glove in accordance with an alternate embodiment of the invention.

FIG. 11 illustrates another glove 1100 according to various embodiments of the invention. Glove 1100 includes alternating patterned/textured sections that correspond with the location of each joint separated by non-patterned/non-textured sections that are ribs to provide extra material when the hand or a finger flexes.

These folds of material (ribs) can be located in any suitable place, including between any two joints, between any fingers, between the thumb and index finger, on the dorsum of the hand and/or on the palm of the hand. The folds can provide any suitable amount of material to permit expansion, and in one embodiment provide between 1/16" and 1/4" of extra material. The folds preferably extend outward away from the hand and/or fingers. In the illustrated example, glove 1100 includes a flexible section 1112 corresponding to the MCP of each finger, a flexible section 1102 corresponding to the PIP of each finger, and a flexible section 1103 corresponding to the DIP of each finger. There is a flexible section 1105 corresponding to the MCP of the thumb and a flexible section 1107 corresponding to the IP of the thumb. There is also a longitudinally oriented pattern 1120 between each of the flexible sections and distal from the DIP joints and IP joint that allows for circumferential expansion of the gloves to minimize biasing forces associated with natural digital circumferential expansion that occurs with normal digital flexion.

Figure 15:
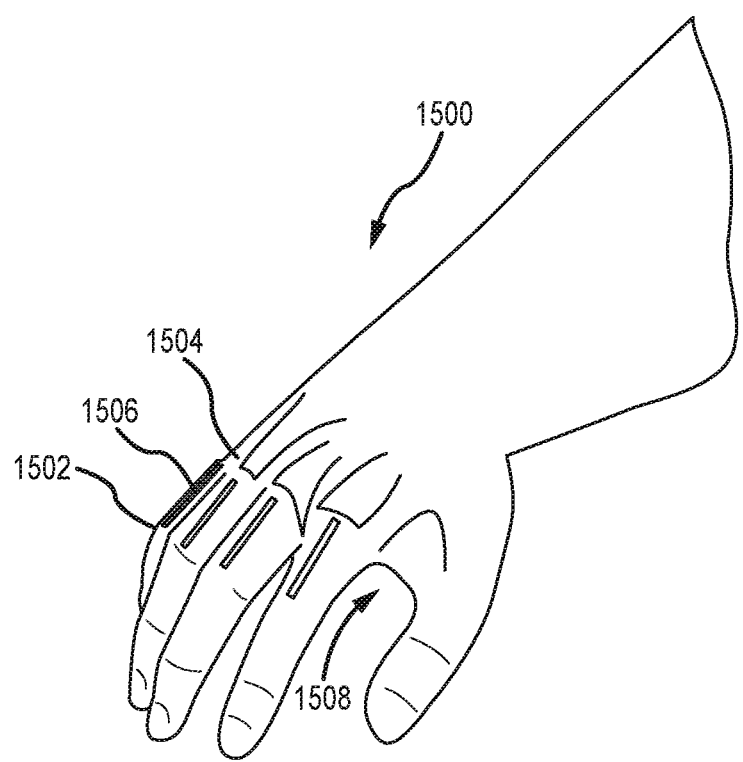
FIG. 15 illustrate another glove having a pattern in accordance with additional embodiments of the invention.
Figure 16B:
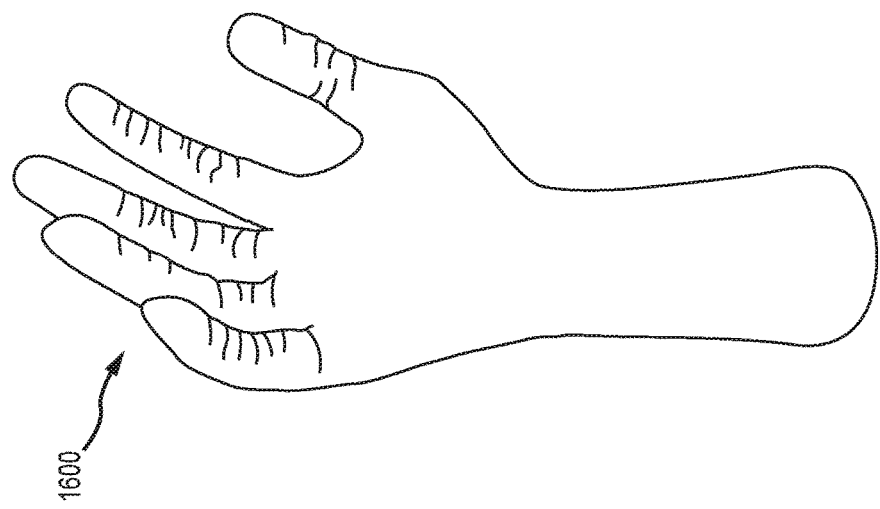
FIGS. 16(*a*) and 16(*b*) illustrate another glove having a pattern in accordance with additional embodiments of the invention.
Figure 16A:
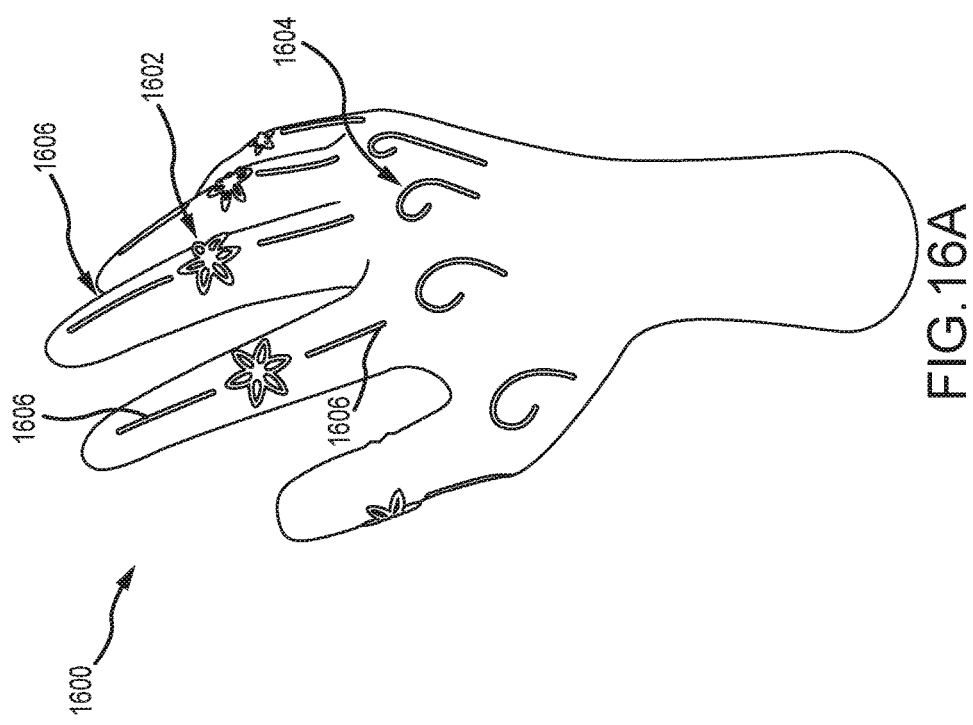
Figures 19A, 19B:
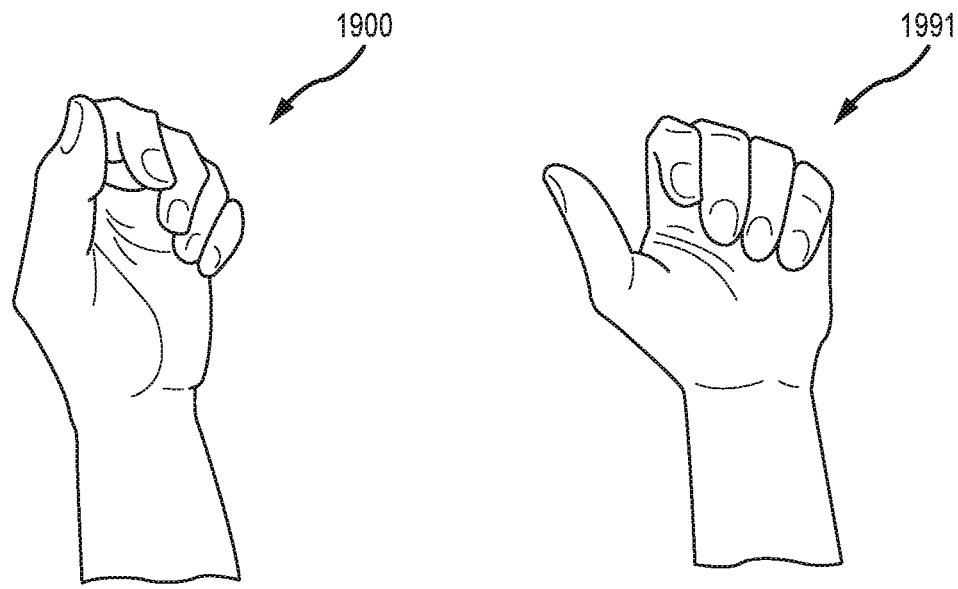
FIG. 19A illustrates a side, perspective view of a hand in a fully relaxed position.
FIG. 19B illustrates a front view of the hand in FIG. 19A.

FIGS. 15 and 16(a) and (b) illustrate additional exemplary gloves 1500 and 1600, respectively. Glove 1500 includes PIP joint modifiers 1502, MCP expansion ridges 1504, a proximal expansion groove 1506, and palm expansion channels 1508 in accordance with exemplary embodiments of the invention.

Glove 1600 includes joint strain relief elements 1602, 1604 and longitudinal expansion relief ridges 1606. Strain relief elements 1602, 1604 can be of any suitable shape that provides a desired amount of stain relief—e.g., greater than or equal to 5%, 10%, 25%, 35%, 50%, or the like. As illustrated, elements 1602, 1604 can be decorative, as long as they provide the desired relief of biasing forces. Similarly, ridges 1606 can provide a desired amount of expansion relief, such as greater than or equal to 5%, 10%, 25%, 35%, 50%, or the like.

Figure 22:
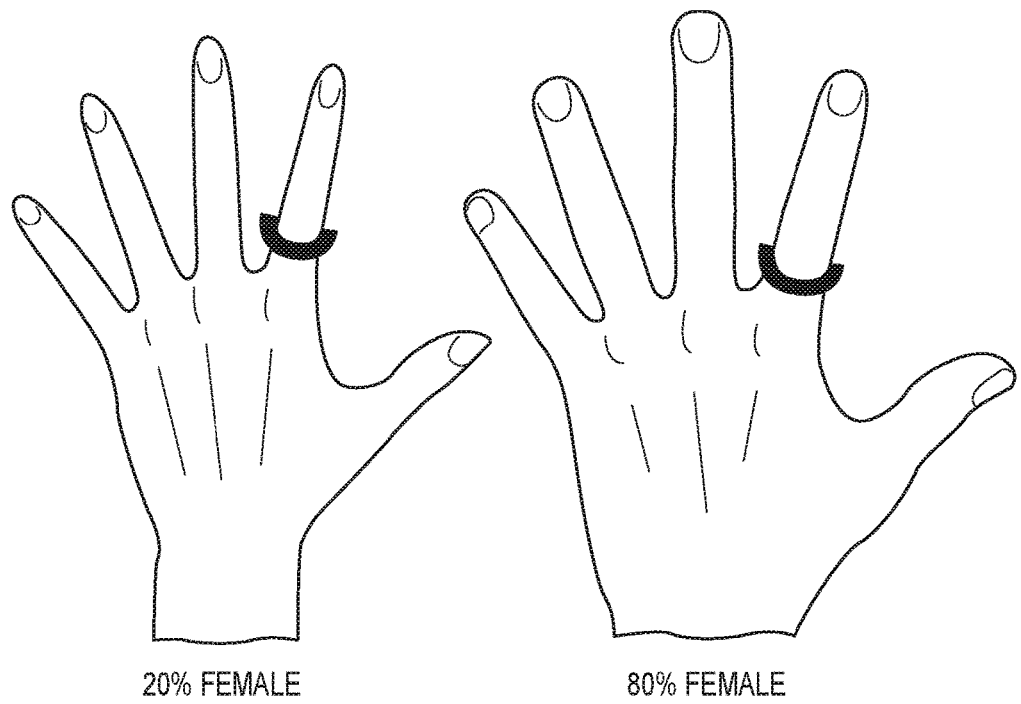
FIG. 22 illustrates a relationship between the circumference of fingers when straight and when flexed.

As previously mentioned, it is also preferred that a glove according to the invention be able to compensate for the expansion of the fingers' respective circumferences when flexed. FIG. 22 illustrates a relationship between the circumferences of fingers when straight and when flexed. A digit circumference can increase from about 15% to about 25% from an extended position to a flex position.

Figure 23:
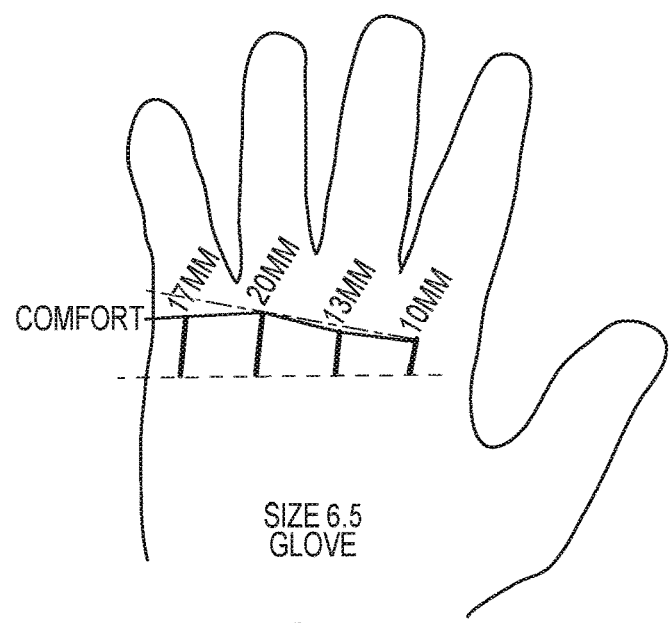
FIG. 23 illustrates an amount of stretch and location of the stretch for a size 6.5 glove at the MCP joints of the fingers.
Figure 24:
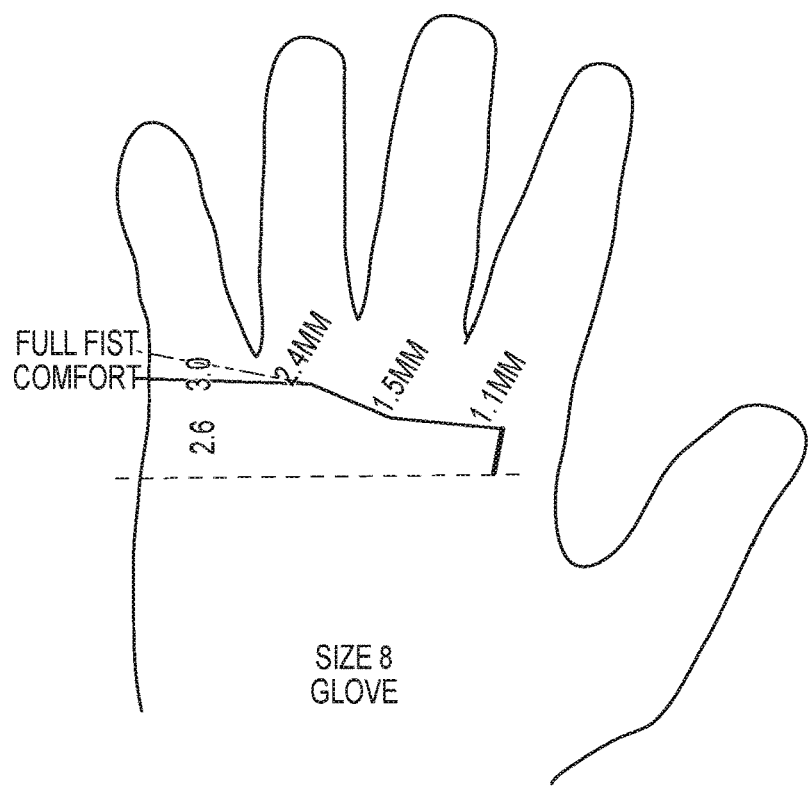
FIG. 24 illustrates an amount of stretch and location of the stretch for a size 8 glove at the MCP joints of the fingers.

FIGS. 23-24 illustrate an amount of stretch and a location for desired stretch in accordance with specific exemplary embodiments of the disclosure. In the illustrated examples, stretch for a size 6.5 glove corresponding to the MCP joints in a hand is illustrated on FIG. 23. Similarly in FIG. 24, an amount of stretch in mm is illustrated for a size 8 glove.

Materials

A glove according to various aspects of exemplary embodiments of the invention can additionally or alternatively include one or both of the following:

The material forming the glove may have varying thicknesses such that thinner portions are used at positions corresponding to one or more joints on a hand (e.g., where joints or the hand are flexed). For example, a thickness can be reduced by 5%, 10%, 25%, 35%, or 50% in any portion of the glove that must flex when the hand and/or one of the digits is opened or closed. For example, the thickness of the material in one or more joint areas or a dorsum region, or at the folds in the palm, or between fingers, or between the thumb and the index finger may be reduced as compared to a thickness of the glove material at other locations.

A glove may be comprised of multiple materials wherein a more flexible material (also called a first material) is used at positions corresponding to joints on a hand (e.g., where the digit joints or the hand are flexed). A less flexible, and preferably more puncture-resistant, material (also called a second material) may be used at other locations. For example, an elongation at break of the more puncture-resistant material can be about 5% or less, 10% or less, 25% or less, 35% or less, 50% or less, 100% or less, 200% or less, 300% or less, 400% or less, or 500% or less than the elongation at break of the more flexible material. Additionally, the first material may stretch by about 10% or more, 25% or more, 50% or more, 100% or more, 200% or more, 300% or more, 400% or more, 500% or more, or 1000% or more than the amount the second material stretches when subjected to the same force to stretch the material, such as about 1/32 pound, 1/16 pound, 1/8 pound, 1/4 pound, 1/2 pound, 1 pound, 2 pounds, or 5 pounds or more. This measurement is made by measuring the stretch of a 1" wide and 6" long piece of material and attaching an appropriate weight about 1/8" below the 6" point of a length of material longer than 6"

and measuring the amount the material is stretched. The second material can be about 0%, 5%, 10%, 25%, 35%, 50%, 100%, 200%, or 300% or more puncture resistant, e.g., as determined according to ASTM F1342, than the first material. The second material may be positioned at one or more finger tips, tip of the thumb, at portions of the palm or dorsum. The first material may be positioned at any of the finger or thumb joints, or the finger tips or any portion of the palm or dorsum, at any suitable location that permits the hand to open and close without much resistance, or where increased tactile sensitivity is desired.

Figure 42A:
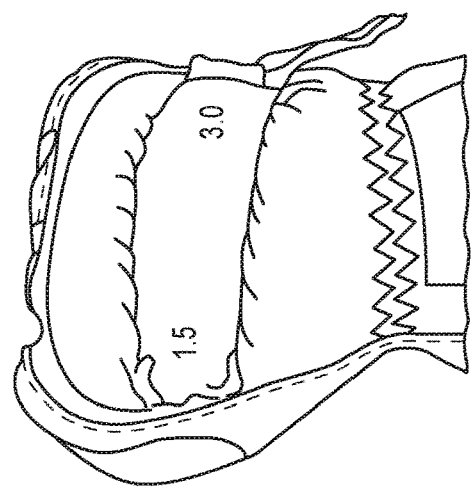
FIGS. 42A-42C depict an experimental glove wherein relatively inflexible material at the dorsum of the hand has been removed and replaced with relatively flexible material.
Figure 42B:
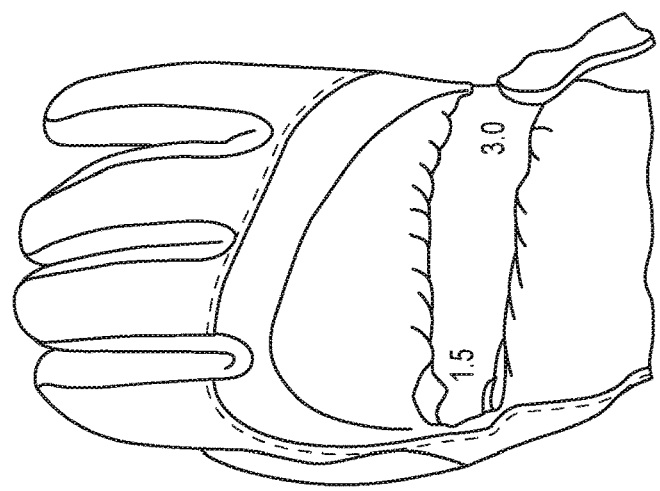
Figure 42C:
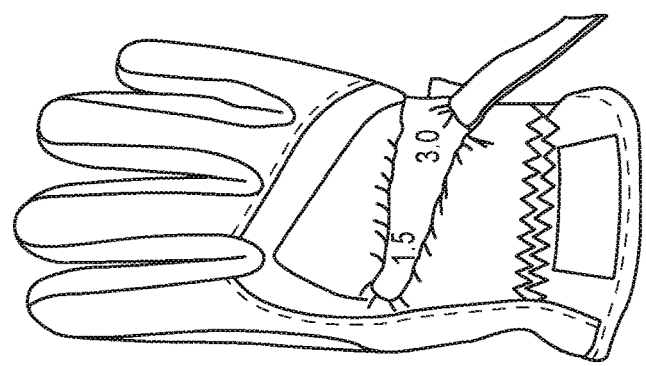
Figure 43:
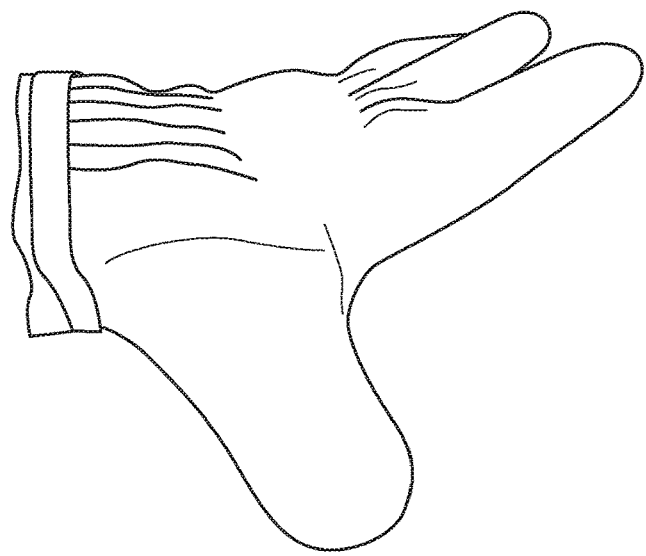
FIG. 43 depicts a known glove with the thumb extended from the index finger.

Examples of such gloves are shown in FIGS. 42A-42C, which depict an experimental glove wherein relatively inflexible material at the dorsum of the hand has been removed and replaced with relatively flexible material. FIG. 45 depicts the glove of FIG. 44 wherein material between the thumb and index finger has been removed to allow for greater or easier extension of the thumb from the index finger. In this example, flexible material, such as Spandex, natural or synthetic rubber, may be used as the first material where the standard cloth glove material has been removed. The second material may be a standard cloth fabric, such as cotton, a synthetic or a mixture of materials.

Figure 49:
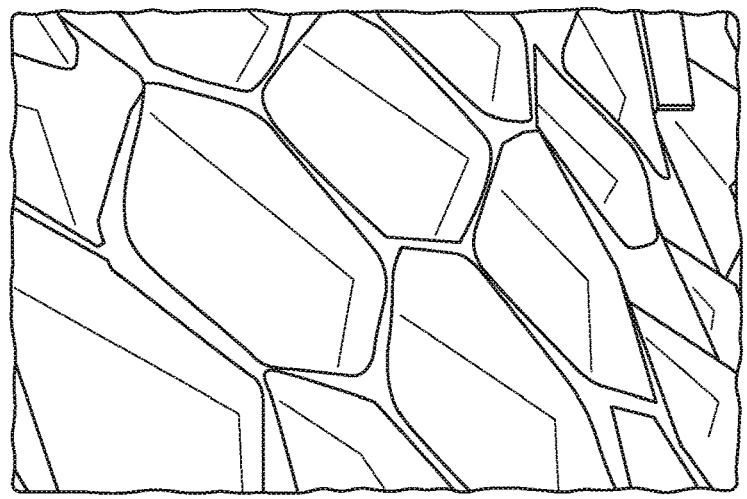
FIG. 49 depicts a flexible material that may be used on a glove according to the invention, wherein the flexible material has pieces of a second, hardened material attached to provide protection to the hand and at the same time permitting the material to stretch.
Figure 50:
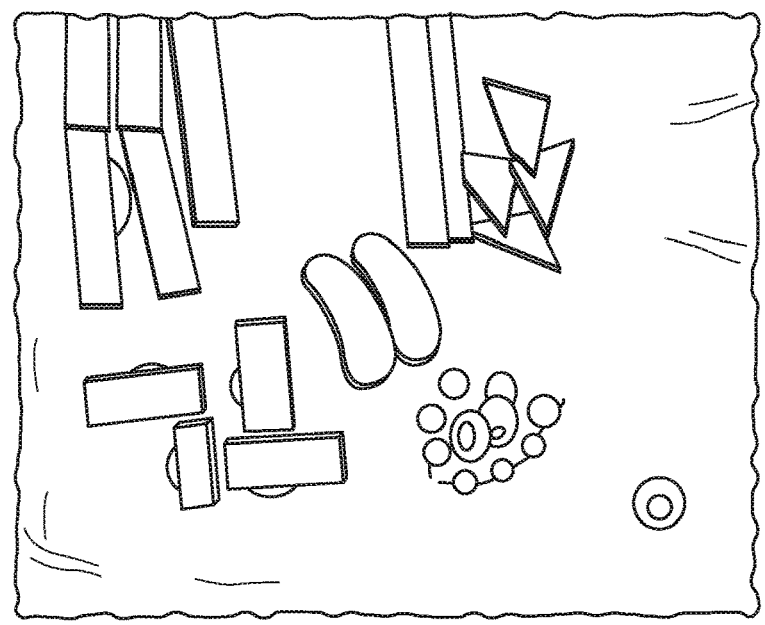
FIG. 50 depicts a flexible material with hard pieces of material attached to it.

FIG. 49 depicts a flexible, second material that may be used on a glove according to the invention, wherein the flexible material has pieces of a second, hardened material (also called cladding) attached to the first material to provide protection to the hand and at the same time permitting the material to stretch. FIG. 50 depicts a section of flat, flexible material with hard pieces of protective material attached to it. The protective material may be twice or more, three times or more, four times or more, five times or more, ten times or more, or twenty times or more harder, as measured using the Shore A or Shore D scales, as the glove material to which it is attached. The protective material may be attached to the glove material in any fashion, such as adhesively, by stitching, heat bonding, or incorporating it between two layers of glove material. In some aspects the protective material is provided in sections that are square, circular, rectangular and/or triangular, although any suitable shape will suffice. In one embodiment, the glove material including the cladding is completely covered by the cladding when in its relaxed position and partly covered by the cladding when stretched. The cladding may also be positioned such that when the glove material is stretched there is no straight line of unprotected glove material that can be sliced with a tool or knife.

Further, a glove according to aspects of the invention, in addition to including any or all of the other features referenced in this application, may include portions where the glove is comprised of materials having the same composition, such as rubber, latex or Spandex, but the thickness of the material varies such that the first material is thinner so that less force is required to stretch the thinner portion. Such a glove may also have portions of material (the second material) thicker than the first material, and potentially thicker than in a standard glove utilizing the same material composition in order to be more resistant to being punctured or to otherwise provide added protection.

Stitching

Figure 44:
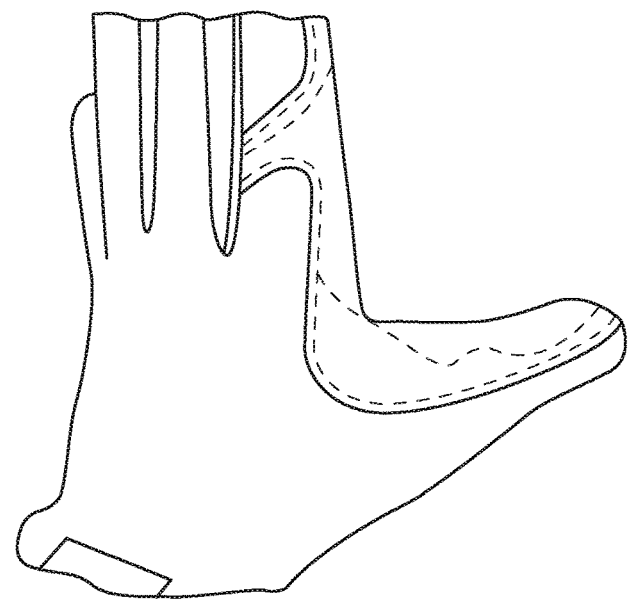
FIG. 44 depicts a modified work glove with zig-zag stitching at the seam extending from the thumb and into the space between the thumb and index finger.
Figure 45:
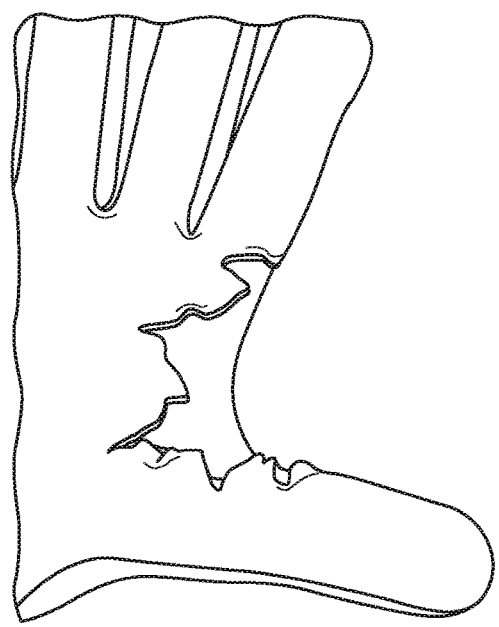
FIG. 45 depicts the glove of FIG. 44 wherein material between the thumb and index finger has been removed to allow for greater or easier extension of the thumb from the index finger.
Figure 46:
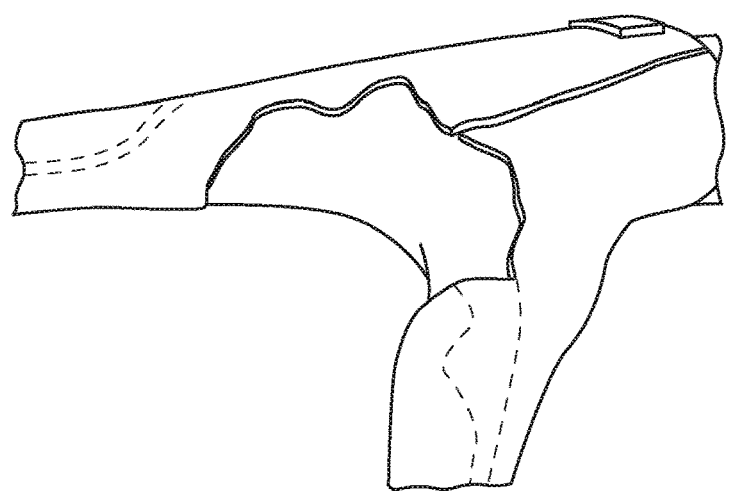
FIG. 46 is a side view of the glove of FIG. 45.
Figure 47A:
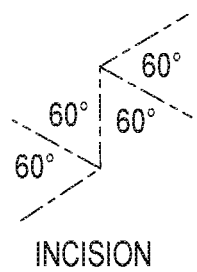
FIGS. 47A-47C depicts a zig-zag stitching pattern that can be utilized on a glove according to aspects of the invention.
Figure 47B:
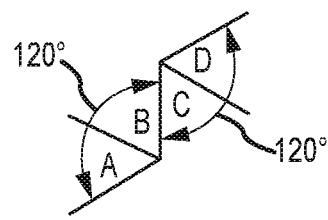
Figure 47C:
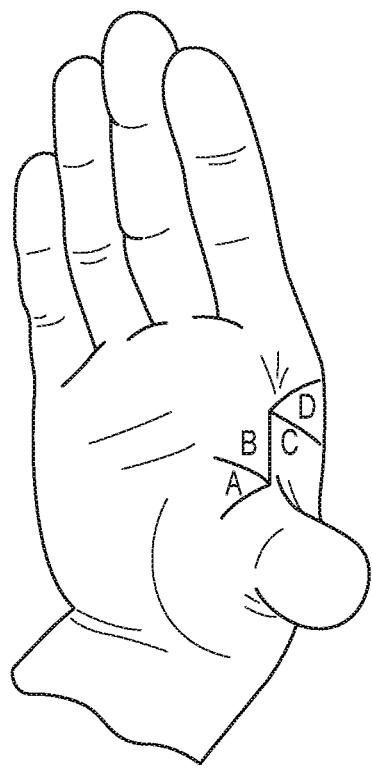
Figure 48A:
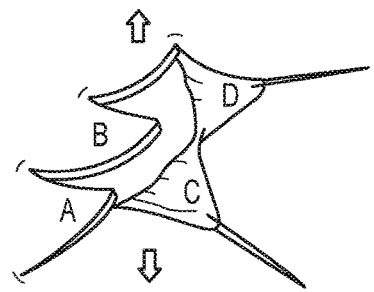
FIGS. 48A-48C depict another zig-zag stitching pattern that can be utilized on a glove according to aspects of the invention.
Figure 48B:
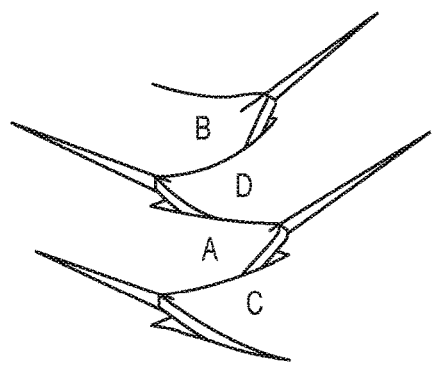
Figure 48C:
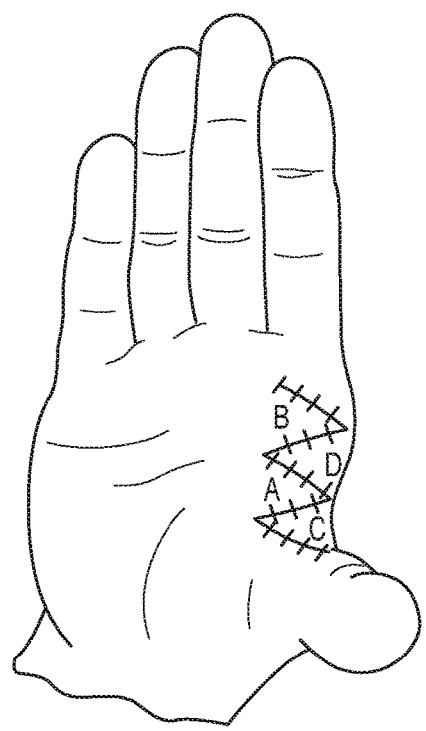

FIGS. 44-46 depict a modified work glove with zig-zag stitching at the seam extending from the thumb and into the space between the thumb and index finger. FIGS. 47A-47C also depict a zig-zag stitching pattern that can be utilized on a glove according to aspects of the invention. FIGS. 48A-48C depict another zig-zag stitching pattern that can be utilized on a glove according to aspects of the invention. The zig-zag stitching, as opposed to standard straight stitching, allows for expansion between fingers or in the area between the thumb and index finger. The zig-zag stitching may be done in any suitable manner, such as at angles from about 50 degrees to 70 degrees, or about 60 degrees, or at angles from about 30 degrees to 45 degrees, or about 45 degrees. Additionally, the thread used to stitch a seam (assuming a glove according to the invention has one or more seams), whether the seam is straight or zig-zag, may be flexible to better allow a hand to move to the open and/or closed position. For example, using the same measuring technique as defined above for the first material, a thread used with aspects of the invention may elongate by either 10% or more, 20% or more, 30% or more, 40% or more, 50% or more, 60% or more, 70% or more, 80% or more, 90% or more, 100% or more, or 200% or more when a weight of either about 1/32 pound, 1/16 pound, 1/8 pound, 1/4 pound, 1/2 pound, 1 pound, 2 pounds, or 5 pounds or more is applied.

Tactile Sensation Enhancement

Figure 51:
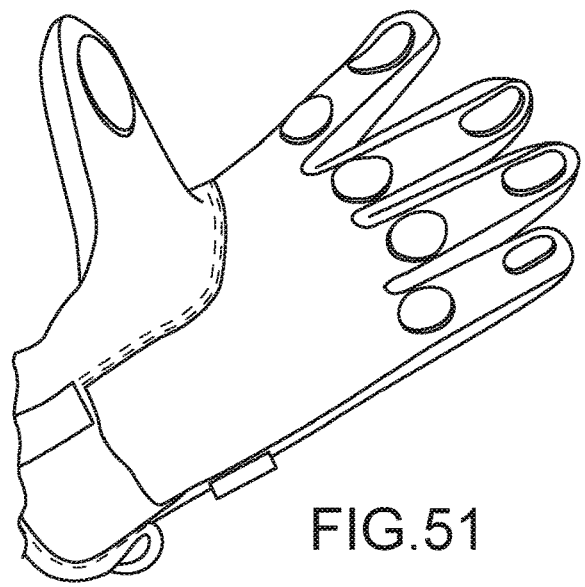
FIG. 51 depicts a glove according to aspects of the invention wherein a material is used at the finger tips and space on the palm region between the MCP joint and PIP joint of each finger to allow for better tactile sensation.
Figure 52:
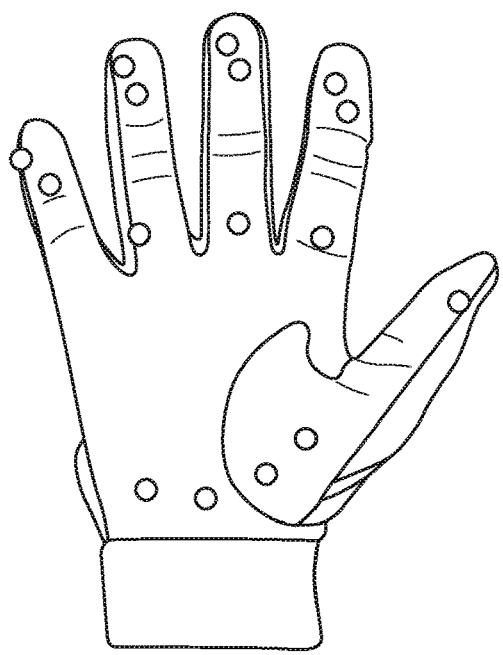
FIG. 52 depicts a glove according to aspects of the invention that has areas enabling better tactile sensation.
Figure 53A:
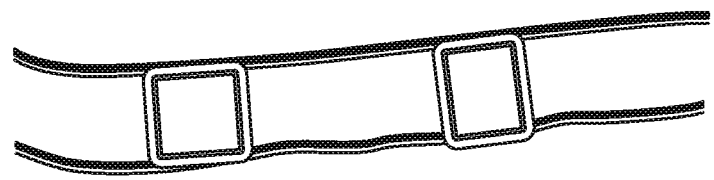
FIG. 53A is a magnified view of a cross section of material that could be used in a glove according to FIG. 53.
Figure 53:
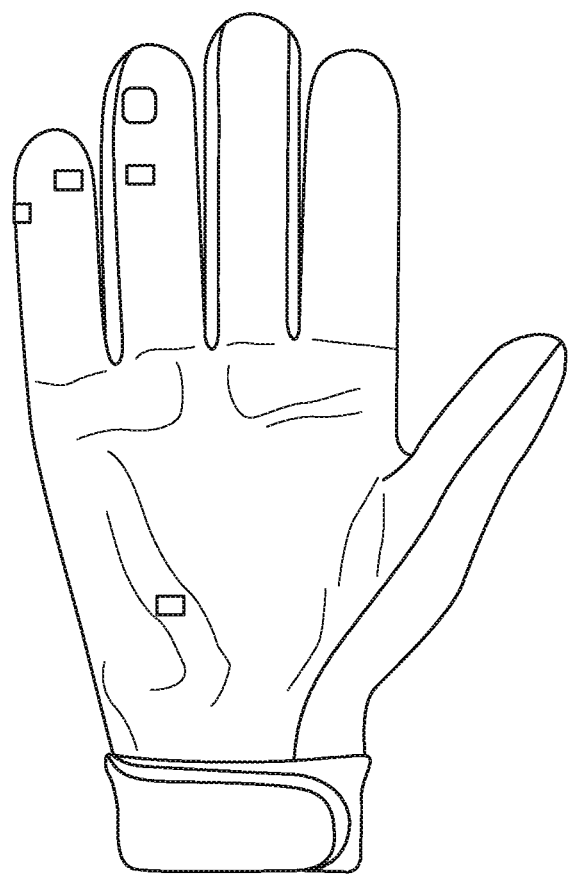
FIG. 53 depicts a glove according to aspects of the invention that has areas enabling better tactile sensation.
Figure 54:
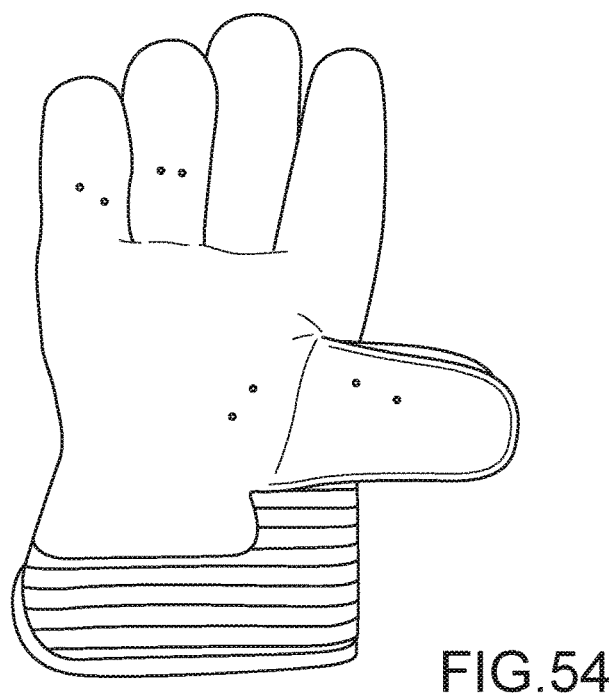
FIG. 54 depicts another glove according to aspects of the invention that has areas enabling better tactile sensation.

FIG. 51 depicts a glove according to aspects of the invention wherein a material is used at the finger tips and space on the palm region between the MCP joint and PIP joint of each finger to allow for better tactile sensation. FIGS. 52 and 53 depict gloves according to aspects of the invention that has areas enabling better tactile sensation. FIG. 53A is a magnified view of a cross section of material that could be used in a glove according to FIG. 53. FIG. 54 depicts another glove according to aspects of the invention that has areas enabling better tactile sensation.

Figure 55:
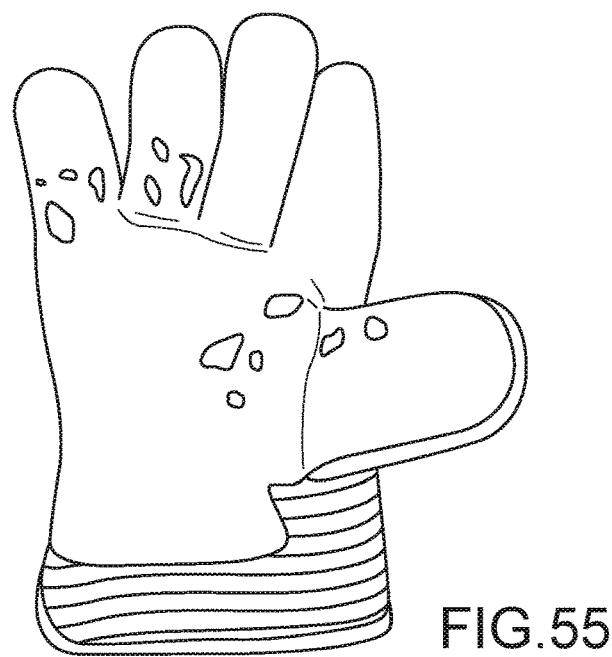
FIG. 55 depicts a standard glove that has had material removed at positions where better tactile sensation is desired.

FIG. 55 depicts a standard glove that has had areas of material removed at positions where better tactile sensation is desired.

Figure 56:
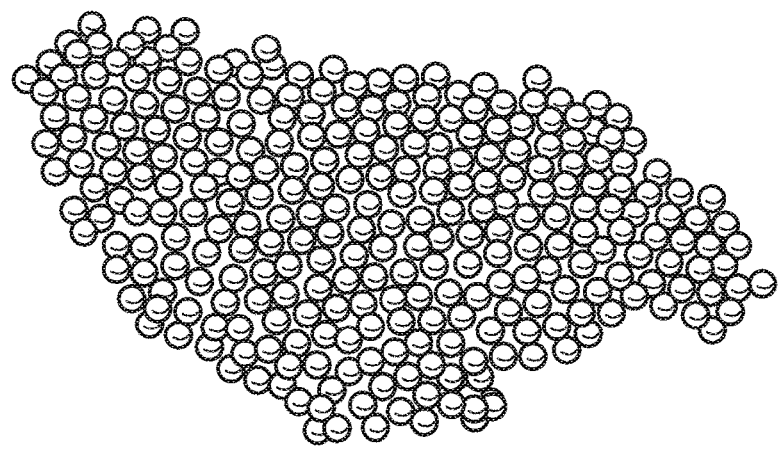
FIG. 56 depicts a standard glove modified to add hardened beads at positions where better tactile sensation is desired.

FIG. 56 depicts a standard glove modified to add hardened beads at positions where better tactile sensation is desired.

Figure 59:
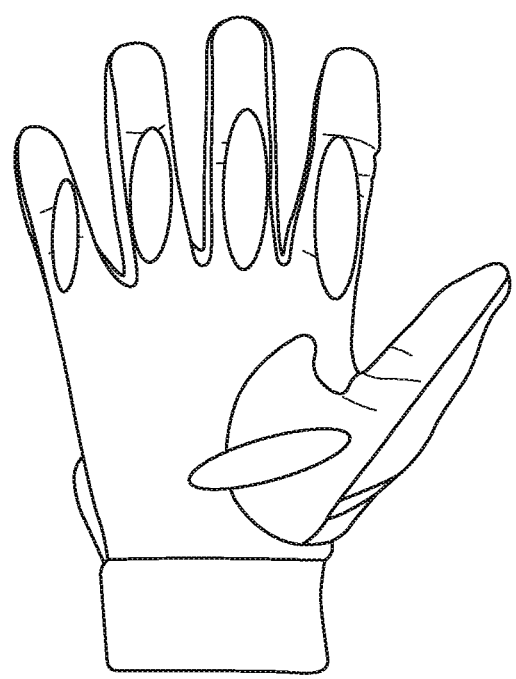
FIG. 59 depicts an alternate embodiment according to aspects of the invention that has a material positioned on the palm side of the fingers and along the muscle of the thumb and palm of the hand to allow for better tactile sensation.

FIG. 59 depicts an alternate embodiment according to aspects of the invention that has a material positioned on the palm side of the fingers and along the muscle of the thumb and palm of the hand to allow for better tactile sensation.

Hardened material (referred to herein as a tactile sensor) may be added to any area of the glove where better tactile sensation is required. The hardened material may be a metal, such as steel or stainless steel, plastic, cardboard, cloth, or any suitable material. It is preferred that the hardened material used for better tactile sensation be at least: twice as hard, three times as hard, four times as hard, five times as hard, six times as hard, seven times as hard, eight times as hard, nine times as hard, ten times as hard, or twenty times as hard, as the adjacent glove material so a user can easily detect through tactile sensation what he/she is touching.

Multiple Gloves

An aspect of the invention also includes the concept of placing one glove (an outer glove) over another (an inner glove) to create a double glove. A double glove could be packaged as one item in a single package thereby eliminating the packaging of the second glove.

The outer glove may be slightly larger than the inner glove in order to facilitate easier placement of one over the other. For instance a size 8 double might include a size 8 inner glove and a size 8.1 outer glove. Additionally, the inner glove may have a micro-texturing on the outside surface and/or the outer glove may have a micro-texturing on the inner surface to facilitate easier placement of one over the other.

Alleviating Slippage Between Layers

Figure 57:
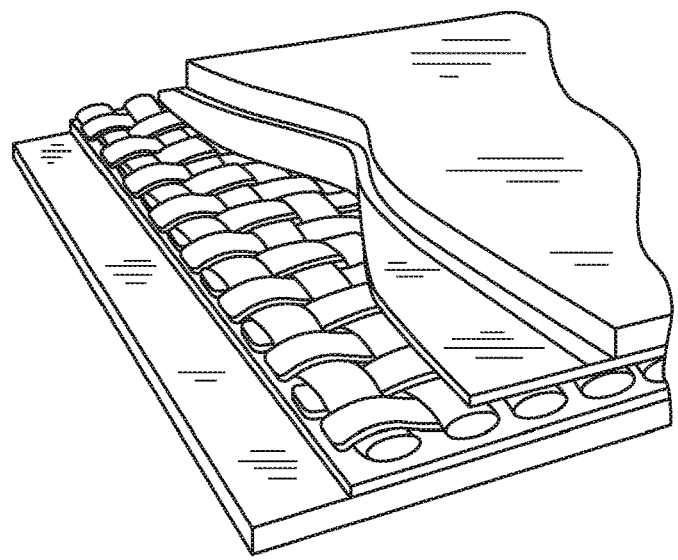
FIG. 57 depicts a cut-away view of a glove comprised of multiple materials, wherein one or more of the materials can slip relative the other materials during use.
Figure 58:
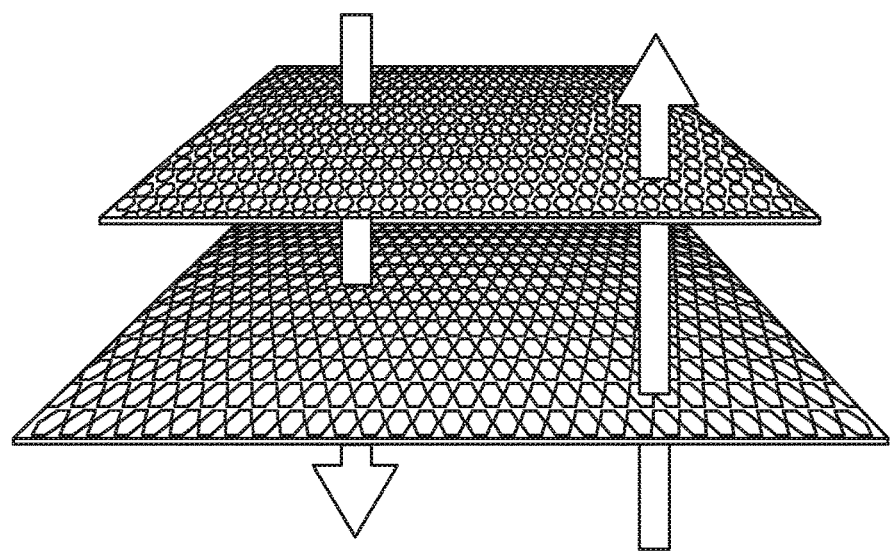
FIG. 58 depicts layers of material according to aspects of the invention that are less prone to slipping relative one another.

FIG. 57 depicts a cut-away view of a glove comprised of multiple materials, wherein one or more of the materials can slip relative the other materials during use. FIG. 58 depicts layers of material according to aspects of the invention that are less prone to slipping relative one another. Any suitable method or structure may be used to reduce or eliminate slippage between glove layer, or multiple gloves, if one glove is worn over another. Adhesives or heat welding may be used. Additionally, interlocking structures on the glove layers may be used. For example, adjacent layers may have raised dimples that interlock when pressed together, or may have raised dimples on one layer that interlock with depressions on an adjacent layer. Or, adjacent layers may have ridges that interlock when pressed together, or may have a combination or ridges and dimples. The raised dimples and/or ridges could be, for example, between 1 mm and 3 mm in height as measured from the surface of the layer.

Some specific, non-limiting examples of a surgical glove according to aspects of the invention are as follows:

1. A glove wherein at least one MCP joint is formed at a flex angle of 10-55°.
2. The glove of example 1 wherein at least two MCP joint portions are formed at a flex angle of 10-45°.
3. The glove of example 1 or 2 wherein at least one MCP joint portion is formed at a flex angle of 15-50°.
4. The glove of any of examples 1-3 wherein at least one MCP joint portion is formed at a flex angle of 20-55°.
5. The glove of any of examples 1-4 wherein at least one PIP joint portion is formed at a flex angle of 5-25°.
6. The glove of any of examples 1-5 wherein at least two PIP joint portions are formed at a flex angle of 5-25°.
7. The glove of any of examples 1-6 wherein at least one PIP joint portion is formed at a flex angle of 10-35°.
8. The glove of any of examples 1-7 wherein at least one PIP joint portion is formed at a flex angle of 15-40°.
9. The glove of any of examples 1-8 wherein at least one DIP joint portion is formed at a flex angle of 5-25°.
10. The glove of any of examples 1-9 wherein at least two DIP joint portions are formed at a flex angle of 5-25°.
11. The glove of any of examples 1-10 wherein at least one DIP joint portion is formed at a flex angle of 10-30°.
12. The glove of any of examples 1-11 wherein at least one DIP joint portion is formed at a flex angle of 15-40°.
13. The glove of any of examples 1-12 wherein the thumb MCP joint portion is formed at a flex angle of 10-45°.
14. The glove of any of examples 1-13 wherein the thumb PIP joint portion is formed at a flex angle of 20-50°.
15. A glove wherein at least one PIP joint is formed at a flex angle of 5-40°.
16. The glove of example 15 wherein at least two PIP joint portions are formed at a flex angle of 5-25°.
17. The glove of any of examples 15 or 16 wherein at least one PIP joint portion is formed at a flex angle of 10-35°.
18. The glove of any of examples 15-17 wherein at least one PIP joint portion is formed at a flex angle of 15-40°.
19. The glove of any of examples 15-18 wherein at least one DIP joint portion is formed at a flex angle of 5-25°.
20. The glove of any of examples 15-19 wherein at least two DIP joint portions are formed at a flex angle of 5-25°.
21. The glove of any of examples 15-20 wherein at least one DIP joint portion is formed at a flex angle of 10-30°.
22. The glove of any of examples 15-21 wherein at least one DIP joint portion is formed at a flex angle of 15-40°.
23. The glove of any of examples 15-22 wherein the thumb MCP joint portion is formed at a flex angle of 10-45°.
24. The glove of any of examples 15-23 wherein the thumb PIP joint portion is formed at a flex angle of 20-50°.
25. A glove wherein at least one DIP joint is formed at a flex angle of 5-25°.
26. The glove of example 25 wherein at least two DIP joint portions are formed at a flex angle of 5-25°.
27. The glove of any of examples 25-26 wherein at least one DIP joint portion is formed at a flex angle of 10-30°.
28. The glove of any of examples 25-27 wherein at least one DIP joint portion is formed at a flex angle of 15-40°.
29. The glove of any of examples 25-28 wherein the thumb MCP joint portion is formed at a flex angle of 10-45°.
30. The glove of any of examples 25-29 wherein the thumb PIP joint portion is formed at a flex angle of 20-50°.
31. A glove wherein the MCP joint of the thumb is formed at a flex angle of 10-45°.
32. The glove of example 31 wherein the PIP joint of the thumb is formed at a flex angle of 20°-50°.
33. The glove of any of examples 1-32 wherein there is a pattern between the MCP joint and PIP joint on at least one finger.
34. The glove of example 33 wherein the pattern is on the top of the at least one finger.
35. The glove of any of examples 1-33 wherein the pattern can expand to provide between 1/16" and 1/4" of extra material to allow for expansion of the finger.
36. The glove of any of examples 33-35 wherein the pattern is a longitudinally-extending rib.
37. The glove of any of examples 33-36 wherein there is a pattern between the MCP joint and PIP joint on a plurality of fingers.
38. The glove of example 37 wherein there is a longitudinally-extending rib between the MCP joint and PIP joint on all four fingers.
39. The glove of any of examples 1-38 wherein there is a pattern between the PIP joint and DIP joint on at least one finger.
40. The glove of claim 39 wherein the pattern is on the top of the at least one finger.
41. The glove of any of examples 39-40 wherein the pattern is a longitudinally-extending rib between the PIP joint and DIP joint.
42. The glove of example 41 wherein the rib is on the top of the at least one finger.
43. The glove of any of examples 39-42 wherein the rib can expand to provide between 1/16" and 1/4" of extra material to allow for expansion of the finger.
44. The glove of any of examples 39-43 wherein there is a pattern between the PIP joint and DIP joint on a plurality of fingers.
45. The glove of example 44 wherein there is a pattern between the PIP joint and DIP joint on all four fingers.
46. The glove of examples 44-45 wherein the pattern is a longitudinally-extending rib.
47. The glove of any of examples 1-46 wherein there is a pattern between the MCP joint on the thumb and the DIP joint of the thumb.
48. The glove of example 47 wherein the pattern is on the top of the thumb.

49. The glove of any of examples 47-48 wherein the pattern can expand to provide between ¹⁄₁₆" and ¼" of extra material to allow for expansion of the thumb.
50. The glove of any of examples 43-49 wherein the pattern is a rib extending along the longitudinal axis between the DIP joint and the IP joint of the thumb.
51. The glove of any of examples 1-50 wherein there is a plurality of patterns, with each pattern located at a different location on the glove.
52. The glove of any of examples 1-51 wherein there is a pattern between the CMC joint and the MCP joint of the thumb.
53. The glove of example 52 wherein the pattern is on the top of the thumb.
54. The glove of any of any of examples 52-53 wherein the pattern can expand to provide between ¹⁄₁₆" and ½" of extra material to allow for flexing of the thumb.
55. The glove of any of examples 52-54 wherein the pattern is a rib along the longitudinal axis between the CMC joint and the MCP joint of the thumb.
56. The glove of any of examples 52-55 wherein there is a plurality of patterns.
57. The glove of any of examples 1-56 that includes an outer surface and an inner surface, and a pattern on at least part of one or more of the outer surface and the inner surface, the pattern for reducing biasing forces when the hand or fingers are moved towards the closed position.
58. The glove of example 57 wherein the pattern also reduces biasing forces when the hand or fingers are moved towards the open position.
59. The glove of any of examples 57 or 58 wherein the pattern is entirely on at least part of the outer surface.
60. The glove of any of examples 57 or 58 wherein the pattern is entirely on at least part of the inner surface.
61. The glove of any of examples 33-60 wherein the pattern is selected from one or more of the group consisting of: (a) ribs, (b) raised portions, wherein the center of each raised portion is no greater than either ¼", ⅛", or ¹⁄₁₆" apart, (c) dimples, or (d) one or more designs.
62. The glove of any of examples 33-61 wherein the pattern is selected from one or more ribs that can provide between ¹⁄₁₆" and ¼" of extra material to allow for expansion while reducing biasing forces, wherein the one or more ribs can be oriented in any direction.
63. The glove of any of examples 33-61 wherein the pattern is selected from alternating raised portions that can collectively provide for ¹⁄₁₆" to ½" of extra material to allow for expansion while reducing biasing forces.
64. The glove of example 63 wherein the raised portions are 10 mm or less in height.
65. The glove of example 63 wherein the raised portions are 5 mm or less in height.
66. The glove of any of examples 63-65 wherein the raised portions have one or more of the following cross-sectional shapes: pyramidal, square, rectangular, semi-oval and semi-circular, and irregular.
67. The glove of any of examples 63-66 wherein each raised portion has a center and the distance between the center of each raised portion is between 1 mm and 10 mm.
68. The glove of any of examples 63-66 wherein each raised portion has a center and the distance between the center of each raised portion is between 2 mm and 5 mm.
69. The glove of example 62 wherein each rib extends 5 mm or less from the outer surface of the glove.
70. The glove of example 62 wherein each rib extends 10 mm or less from the outer surface of the glove.
71. The glove of example 61 wherein the one or more designs are selected from the group consisting of: (a) flowers, (b) letters, (c) concentric circles, (d) numbers, and (e) random designs.
72. The glove of any of examples 1-32 that includes patterns, wherein the patterns provide additional material to permit flexion of the hand while reducing biasing forces, the patterns being at one or more of the following positions on the glove: (a) portions corresponding to one or more of the MCP joints, (b) portions corresponding to one or more of the PIP joints, (c) portions corresponding to one or more of the DIP joints, (d) a portion corresponding to the space between the thumb and index finger, (e) portions corresponding to one or more spaces between any of the fingers, (f) a portion corresponding to at least part of the palm of the hand, and (g) a portion corresponding to at least part of the dorsum of the hand.
73. The glove of any of examples 1-72 wherein the pattern is formed on the dorsum side and/or the palm side of one or more of the following: the MCP joint of the index finger, the MCP joint of the middle finger, the MCP joint of the ring finger, and the MCP joint of the little finger.
74. The glove of any of examples 33-73 wherein the pattern is formed on the dorsum side and/or the palm side of one or more of the following: the PIP joint of the index finger, the PIP joint of the middle finger, the PIP joint of the ring finger, and the PIP joint of the little finger.
75. The glove of any of examples 33-74 wherein the pattern is formed on the dorsum side and/or the palm side of one or more of the following: the DIP joint of the index finger, the DIP joint of the middle finger, the DIP joint of the ring finger, and the DIP joint of the little finger.
76. The glove of any of examples 33-75 wherein the pattern is formed on the dorsum side and/or the palm side of the CMC joint of the thumb.
77. The glove of any of examples 33-76 wherein the pattern is formed on the dorsum side and/or the palm side of the MCP joint of the thumb.
78. The glove of any of examples 33-77 wherein the pattern is formed on the dorsum side and/or the palm side of the PIP joint of the thumb.
79. The glove of any of examples 33-78 wherein the pattern is formed between the thumb and index finger.
80. The glove of any of examples 33-79 wherein the pattern is formed between the index finger and middle finger.
81. The glove of any of examples 33-80 wherein the pattern is formed between the middle finger and ring finger.
82. The glove of any of examples 33-81 wherein the pattern is formed between the ring finger and little finger.
83. The glove of any of examples 33-82 wherein the pattern is formed on at least part of the palm of the hand.
84. The glove of any of examples 33-83 wherein the pattern is formed on at least part of the dorsum of the hand.

85. The glove of any of examples 33-84 wherein the pattern is formed on the palm and extends from approximately the center of the palm to the area between the thumb and index finger.
86. The glove of any of examples 33-85 wherein the pattern is formed on the entire palm of the hand.
87. The glove of any of examples 33-86 wherein the pattern is formed on the dorsum behind the little finger and ring finger.
88. The glove of any of examples 33-87 wherein the pattern is formed on the dorsum behind the little finger, the ring finger and the middle finger.
89. The glove of any of examples 33-88 wherein the pattern is formed on the dorsum behind all of the fingers, and extends at least ¼" from the MCP joints.
90. The glove of any of examples 33-89 wherein the pattern is formed on the dorsum behind all of the fingers and the thumb, and extends at least ¼" from the MCP joints on the fingers.
91. The glove of any of examples 87-90 wherein the pattern expands in width the closer it is to the little finger, and has a minimum width of at least ¼" from the MCP joint on the index finger.
92. The glove of any of examples 1-91 that is formed at a flex angle in the palm region.
93. The glove of any of examples 1-92 wherein the glove is formed at a 5-25° flex angle in the palm region.
94. The glove of any of examples 1-92 wherein the glove is formed at a 10-40° flex angle at the palm.
95. The glove of any of examples 33-91 wherein the pattern covers the index finger on the dorsum and/or palm side from the distal hand to the proximal phalanx.
96. The glove of any of examples 33-95 wherein the pattern covers the dorsum and/or the palm side of the little finger.
97. The glove of any of examples 33-96 wherein the pattern covers the dorsum side of each finger.
98. The glove of any of examples 33-97 wherein the pattern covers the palm side of each finger.
99. The glove of any of examples 33-98 wherein the pattern covers the dorsum side and/or the palm side of the thumb.
100. The glove of any of examples 72-99 wherein the pattern comprises one or more of the group selected from: (a) ribs, (b) raised portions, wherein the center of each raised portion is no greater than either ¼", ⅛", or 1/16" apart, (c) dimples, or (d) one or more designs.
101. The glove of example 100 wherein the raised portions comprise one or more of the group selected from: the one or more designs are selected from the group consisting of: (a) flowers, (b) letters, (c) concentric circles, (d) numbers, and (e) random designs.
102. The glove of any of examples 33-101 wherein each pattern present on a finger provides between 1/16" and ⅜" of additional material to reduce biasing force during flexion.
103. The glove of any of examples 33-102 wherein each pattern present on the dorsum provides between ⅛" and ½" of additional material to reduce biasing force during flexion.
104. The glove of any of examples 33-103 wherein each pattern present on the palm provides between ⅛" and ½" of additional material to reduce biasing force during flexion.
105. The glove of any of examples 33-104 wherein a pattern present between the thumb and index finger provides between ¼" and ½" of additional material to reduce biasing force during flexion.
106. The glove of any of examples 33-105 wherein a pattern present between any two fingers provides between 1/16" and ½" of additional material to reduce biasing force during flexion.
107. A glove with portions formed as follows: (a) a MCP joint of the index finger has a flex angle of 10°-30°, and (b) a PIP joint portion on the same finger is formed at a flex angle greater than the flex angle at which the MCP joint portion is formed.
108. The glove of example 107 wherein the PIP joint portion is formed at a flex angle of between 30° and 45°.
109. The glove of example 107 or 108 that includes a DIP joint portion on the same finger formed at a flex angle of less than the flex angle of the MCP joint.
110. The glove of example 110 wherein the DIP joint portion is formed at a flex angle of 0°-20°.
111. The glove of any of examples 107-110 wherein the flex angle of the MCP joint portion is 25°.
112. The glove of any of examples 107-111 wherein the flex angle of the PIP joint portion is 40°.
113. A glove with portions formed as follows: (a) a MCP joint portion of the middle finger has a flex angle of 10°-30°, and (b) a PIP joint portion on the same finger formed at a flex angle greater than the flex angle at which the MCP joint portion is formed.
114. The glove of example 113 wherein the PIP joint portion is formed at a flex angle of between 30° and 45°.
115. The glove of any of examples 113 or 114 wherein the finger includes a DIP joint formed at a flex angle of less than the flex angle of the MCP joint portion.
116. The glove of example 115 wherein the DIP joint portion is formed at a flex angle of 0°-20°.
117. The glove of any of examples 113-116 wherein the flex angle of the MCP joint portion is 25°.
118. The glove of any of examples 113-117 wherein the flex angle of the PIP joint portion is 40°.
119. A glove with portions formed as follows: (a) a MCP joint of the ring finger has a flex angle of 10°-30°, and (b) a PIP joint portion is formed at a flex angle greater than the flex angle at which the MCP joint portion is formed.
120. A glove with portions formed as follows: (a) a MCP joint of the little finger has a flex angle of 10°-30°, and (b) a PIP joint is formed at a flex angle greater than the flex angle at which the MCP joint portion is formed.
121. The glove of example 119 or 120 wherein the PIP joint portion is formed at a flex angle of between 30° and 45°.
122. The glove of example 119 or 120 wherein the DIP joint portion is formed at a flex angle of less than the flex angle of the MCP joint portion.
123. The glove of any of examples 119 or 120 that includes a DIP joint portion formed at a flex angle of 0°-20°.
124. The glove of any of examples 119-123 wherein the flex angle of the MCP joint portion is 25°.
125. The glove of any of examples 119-124 wherein the flex angle of the PIP joint portion is 40°.
126. The glove of any of examples 119-124 that further includes patterns to assist to alleviating the biasing forces associated with one or more of: (a) closing the hand, (b) opening the hand, (c) flexing or bending the fingers, or (d) moving the thumb.

127. A glove having an index finger portion, a middle finger portion, a ring finger portion, a little finger portion and a thumb portion wherein:
   (a) the section of the index finger portion corresponding to the index finger PIP joint is at an angle; and
   (b) the section of the middle finger portion corresponding to the middle finger PIP joint is formed at an angle equal to or greater than the angle of the section of the index finger portion corresponding to the index finger PIP joint.
128. A glove having an index finger portion, a middle finger portion, a ring finger portion, a little finger portion, a thumb portion, a palm portion and a dorsum portion, wherein one or more of part or all of either the index finger portion, ring finger portion, thumb portion, palm portion or dorsum portion is formed of a first material having a lower durometer and being more flexible than a second material that forms the rest of the glove.
129. The glove of example 128 that further includes one of the structures as set forth in examples 1-127 or 130-144.
130. A glove having an index finger portion, a middle finger portion, a ring finger portion, a little finger portion, a thumb portion, a palm portion and a dorsum portion, wherein one or more of part or all of either the index finger portion, ring finger portion, thumb portion, palm portion or dorsum portion is formed of a first material having a lower durometer and being more flexible than a second material that forms the rest of the glove.
131. The glove of example 130 that further includes one of the structures as set forth in examples 1-127 or 133-144.
132. The glove of either of examples 130 or 131 wherein the thinner portion(s) are between 10° and 50° thinner than the thicker portions.
133. A glove wherein one or more of the following portions is formed as follows: (a) the portion corresponding to the DIP joint of the index finger is formed at a 5-25° flex angle, (b) the portion corresponding to the DIP joint of the middle finger is at a 5-25° flex angle, (c) the portion corresponding to the DIP joint of the ring finger is formed at a 10-30° flex angle, and (d) the portion corresponding to the DIP joint of the little finger is formed at a 15-40° flex angle.
134. The glove of example 133 wherein one or more of the following portions is formed as follows: (a) the portion corresponding to the MCP joint of the thumb is formed at a flex angle of 10-45°, and (b) the portion corresponding to the PIP joint of the thumb is formed at a flex angle of 20-50°.
135. The glove of any of examples 133-134 wherein one or more of the following portions is formed as follows: (a) the portion corresponding to the MCP joint of the thumb is formed at a flex angle of 10-45°, and (b) the portion corresponding to the PIP joint of the thumb is formed at a flex angle of 20-50°.
136. The glove of any of examples 133-135 wherein the portion corresponding to the CMC joint of the thumb is formed at a flex angle of 5-25°.
137. The glove of any of examples 133-136 wherein the thumb CMC joint is positioned such that the entire thumb axis is positioned in its relaxed plane.
138. The glove of example 137 wherein the thumb is abducted out of the plane of the palm in a partially opposed position to the plane of the palm.
139. The glove of any of examples 133-138 wherein the flex angle of the DIP joint is less than the flex angle of the corresponding MCP joint.
140. The glove of example 36 wherein the rib is on the top surface of the finger.
141. The glove of example 38 wherein each rib is on the top surface of the finger.
142. The glove of example 46 wherein each rib can provide between 1/16" and 1/4" of extra material.
143. A glove formed at the natural cascading position shown in FIG. 21 plus or minus 10° for each flex angle.
144. The glove of any of examples 133-143 that further includes one or more patterns.
145. A glove wherein the flex angle of the portions of the glove corresponding to the MCP joint of each of the index finger, middle finger, ring finger and little finger is 40°-50°.
146. A glove wherein the flex angle of portions of the glove corresponding to the MCP joint of at least one of the index finger, middle finger, ring finger and/or little finger is 40°-50°.
147. The glove of any of examples 145-146 wherein the flex angle of the portions of the glove corresponding to the PIP joint of each of the index finger, middle finger, ring finger and little finger is 10°-20°.
148. The glove of any of examples 145-146 wherein the flex angle of one or more portions of the glove corresponding to the PIP joint of each index finger, middle finger, ring finger and/or little finger is 10°-20°.
149. The glove of any of examples 145-148 wherein the flex angle of the portions of the glove corresponding to the DIP joint of each of the index finger, middle finger, ring finger and little finger is 5°-25° or 10°-20°.
150. The glove of any of examples 145-148 wherein the flex angle of one or more portions of the glove corresponding to the DIP joint of one or more of the index finger, middle finger, ring finger and/or little finger is 5°-25° or 10°-20°.
151. The glove of any of examples 1-150 that is formed to provide an additional 8 mm-15 mm of material along the length of the top surface of the index finger as compared to the length of the top surface of the index finger when in its extended position and straight.
152. The glove of any of examples 1-151 that is formed to provide an additional 10 mm-18 mm of material along the length of the top surface of the middle finger as compared to the length of the top surface of the middle finger when in its extended position and straight.
153. The glove of any of examples 1-152 that is formed to provide an additional 15 mm-30 mm of material along the length of the top surface of the ring finger as compared to the length of the top surface of the ring finger when in its extended position and straight.
154. The glove of any of examples 1-153 that is formed to provide an additional 20 mm-40 mm of material along the length of the top surface of the little finger as compared to the length of the top surface of the little finger when in its extended position and straight.
155. The glove of any of examples 151-154 wherein 40°-60° of the additional material is provided by flex angles at one or more joints of the finger.
156. The glove of example 155 wherein the remaining extra material is provided by patterns at one or more joints of the finger.

157. The glove of any of examples 151-154 wherein all of the additional material is provided by the flex angles at one or more joints of the finger.
158. The glove of any of examples 151-154 wherein all of the additional material is provided by patterns at one or more joints of the finger.
159. The glove of any of examples 156-158 wherein the extra material provided by patterns is provided such that 40-60% of the extra material is at the MCP joint.
160. The glove of any of examples 151-159 wherein 20-30% of the extra material is at the DIP joint.
161. The glove of any of examples 156-160 wherein all of the patterns are ribs.
162. The glove of any of examples 1-161 wherein there are four separate, non-connected ribs at the thumb PIP joint.
163. The glove of any of examples 1-162 wherein there are at least four separate, non-connected ribs at the index finger MCP joint.
164. The glove of any of examples 1-163 wherein there are at least six separate, non-connected ribs at the MCP joint of the middle finger and index finger.
165. The glove of any of examples 1-164 wherein there are at least seven separate, non-connected ribs at the MCP joint of the little finger.
166. The glove of any of examples 1-165 wherein there are at least three separate, non-connected ribs in the palm portion.
167. The glove of example 166 wherein the uppermost rib in the palm portion extends from at least under the index finger to under the little finger.
168. The glove of any of examples 166-167 wherein the center rib of the palm portion extends from at least the index finger to a location between the little finger and ring finger.
169. The glove of any of examples 166-168 wherein the lower rib of the palm portion extends at least from the index finger to under the ring finger.
170. The glove of any of examples 166-169 wherein at least one rib of the palm portion extends into the space between the thumb and index finger.
171. The glove of any of examples 1-170 that further includes a rib extending along the muscle of the thumb.
172. The glove of any of examples 1-171 wherein there are three separate, non-connected ribs at one or more of the thumb IP joint, the index finger DIP joint, the middle finger DIP joint, the ring finger DIP joint, the little finger DIP joint, the index finger PIP joint, the middle finger PIP joint, the ring finger PIP joint, and the little finger PIP joint.
173. The glove of example 172 wherein the ribs extend completely around the joint.
174. The glove of any of examples 162-165 wherein each rib is curved and the center of each rib is 1 mm-3 mm farther from the distal end of the finger than at least one end of the rib.
175. The glove of any of examples 162-165 and 174 wherein the ribs are only positioned on the top of the MCP joint.
176. The glove of any of examples 1-175 wherein the portion located at the MCP joint of the index finger provides 2 mm-15 mm or 2 mm-11 mm of extra material.
177. The glove of any of examples 1-176 wherein the portion located at the MCP joint of the middle finger provides 3 mm-20 mm or 3 mm-15 mm of extra material.
178. The glove of any of examples 1-177 wherein the portion located at the MCP joint of the ring finger provides 4 mm-25 mm or 4 mm-24 mm of extra material.
179. The glove of any of examples 1-178 wherein the portion located at the MCP joint of the little finger provides 5 mm-30 mm or 5 mm-35 mm of extra material.
180. The glove of any of examples 1-179 wherein the portion located at the PIP joint of the index finger provides 1 mm-8 mm or 1 mm-10 mm of extra material.
181. The glove of any of examples 1-180 wherein the portion located at the DIP joint of the index finger provides 1 mm-8 mm or 1 mm-10 mm of extra material.
182. The glove of any of examples 1-181 wherein the portion located at the PIP joint of the middle finger provides 1 mm-8 mm or 1 mm-10 mm of extra material.
183. The glove of any of examples 1-182 wherein the portion located at the DIP joint of the middle finger provides 1 mm-8 mm or 1 mm-10 mm of extra material.
184. The glove of any of examples 1-183 wherein the portion located at the PIP joint of the ring finger provides 1 mm-8 mm or 1 mm-10 mm of extra material.
185. The glove of any of examples 1-184 wherein the portion located at the PIP joint of the ring finger provides 1 mm-8 mm or 1 mm-10 mm of extra material.
186. The glove of any of examples 1-185 wherein the portion located at the PIP joint of the little finger provides 1 mm-8 mm or 1 mm-10 mm of extra material.
187. The glove of any of examples 1-186 wherein the portion located at the thumb PIP joint provides 5 mm-20 mm of extra material.
188. The glove of any of examples 1-187 wherein the portion located at the thumb IP joint provides 8 mm-20 mm of extra material.
189. The glove of any of examples 1-188 wherein a pattern between any of the fingers provides 20 mm-200 mm of extra material.
190. The glove of any of examples 1-189 wherein a pattern between the index finger and thumb provides 30 mm-350 mm of extra material.
191. The glove of any of examples 175-190 wherein the extra material is provided by a pattern.
192. The glove of any of examples 175-190 wherein the extra material is provided by the shape of the glove.
193. The glove of any of examples 175-190 wherein the extra material is provided by a combination of a pattern and the shape of the glove.
194. The glove according to any of examples 1-193 wherein the thickness of the material forming the glove is reduced by 5%-50% at one or more of the following positions: (a) at least one MCP joint of the fingers, (b) at least one PIP joint of the fingers, and (c) at least one DIP joint of the fingers.
195. The glove according to any of examples 1-194 wherein the thickness of the material forming the glove is reduced by 5%-50% at one or more of the following positions: (1) the PIP joint of the thumb, and (b) the IP joint of the thumb.

196. The glove according to any of examples 1-195 wherein the thickness of the material forming the glove is reduced by 5%-50% at one or more of the following positions: (a) the palm, and (b) at least one of the spaces between any two fingers and/or the index finger and thumb.

197. The glove according to any of examples 1-196 that includes a first material and a second material, wherein the second material is 50%-300% or more puncture resistant than the first material as measured according to ASTM F1342, and the second material is positioned at one or more of the finger tips and tip of the thumb.

198. The glove according to example 197 wherein the second material is positioned on the palm side of one or more fingers between the finger joints.

199. The glove according to either of examples 197-198 wherein the second material is positioned on the palm side of the thumb between the joints.

200. The glove according to any of examples 197-199 wherein the second material is positioned on the palm and extends ¼" or more from the MCP joint of each finger towards the center of the palm.

201. The glove according to any of examples 197-200 wherein the second material is positioned on the palm region of the muscle of the thumb.

202. The glove according to example 161 wherein there are between 2-5 separate, non-connected ribs at the thumb PIP joint.

203. The glove according to any of examples 161 or 202 wherein there are between 2-6 separate, non-connected ribs at the index finger MCP joint.

204. The glove according to any of examples 161 or 202-203 wherein there are between 2-6 separate, non-connected ribs at the middle finger MCP joint.

205. The glove according to any of examples 161 or 202-204 wherein there are between 2-7 separate, non-connected ribs at the ring finger MCP joint.

206. The glove according to any of examples 161 or 202-205 wherein there are between 2-8 separate, non-connected ribs at the little finger MCP joint.

207. The glove of any of examples 1-165 or 202-206 wherein there are between 1 and 5 separate, non-connected ribs in the palm portion of the glove.

208. The glove of any of examples 1-171 wherein there are 2-5 separate, non-connected ribs at one or more of the thumb IP joint, the index finger DIP joint, the middle finger DIP joint, the ring finger DIP joint, the little finger DIP joint, the index finger PIP joint, the middle finger PIP joint, the ring finger PIP joint, and the little finger PIP joint.

209. The glove of any of examples 1-208 that includes one or more tactile sensors along the palm and/or palm region of at least one digit.

210. The glove of example 209 that includes one or more tactile sensors at one or more fingertip portions.

211. The glove of any of examples 209-210 that includes tactile sensors at each fingertip portion.

212. The glove of any of examples 209-211 that includes one or more tactile sensors at the palm side tip of the thumb portion.

213. The glove of any of examples 209-212 that includes one or more tactile sensors at one or more positions on the palm portion.

214. The glove of any of examples 209-213 that includes one or more tactile sensors on one or more portions of the palm side of at least one digit between (a) the MCP joint and PIP joint of the index finger, middle finger, ring finger or little finger, (b) the PIP joint and DIP joint of the index finger, middle finger, ring finger or little finger, and/or (c) the IP joint and DIP joint of the thumb.

215. The glove of example 214 that includes one or more tactile sensors between the MCP joint and PIP joint of at least one finger.

216. The glove of any of examples 214-215 that includes one or more tactile sensors between the PIP joint and DIP joint of at least one finger.

217. The glove of any of examples 214-216 that includes one or more tactile sensors between the thumb IP joint and DIP joint.

218. The glove of any of examples 214-217 that includes one or more tactile sensors between the MCP joint and PIP joint of each finger.

219. The glove of example 218 that includes one or more tactile sensors between the IP joint and DIP joint of the thumb.

220. The glove of any of examples 209-219 wherein each of the tactile sensors is at least twice as hard as the glove material surrounding it as measured on either the Shore A or Shore D scale.

221. The glove of any of examples 209-219 wherein each of the tactile sensors is at least three times as hard as the glove material surrounding it as measured on either the Shore A or Shore D scale.

222. The glove of any of examples 209-219 wherein each of the tactile sensors is at least four times as hard as the glove material surrounding it as measured on either the Shore A or Shore D scale.

223. The glove of any of examples 209-219 wherein each of the tactile sensors is at least five times as hard as the glove material surrounding it as measured on either the Shore A or Shore D scale.

224. The glove of any of examples 209-219 wherein each of the tactile sensors is at least ten times as hard as the glove material surrounding it as measured on either the Shore A or Shore D scale.

225. The glove of any of examples 209-224 wherein each of the tactile sensors are comprised of plastic and the glove material surrounding each tactile sensor is comprised of cloth, spandex or rubber.

226. The glove of any of examples 209-224 wherein each of the tactile sensors is comprised of metal.

227. The glove of example 226 wherein the metal is steel.

228. The glove of example 226 wherein the metal is stainless steel.

229. The glove of any of examples 209-224 wherein each of the tactile sensors is comprised of either plastic or metal.

230. The glove of any of examples 209-224 wherein at least one of the tactile sensors is comprised of cloth.

231. The glove of example 230 wherein each tactile sensor that is comprised of cloth is surrounded by one or more of (a) a second cloth, or (b) a natural or synthetic rubber.

232. The glove of any of examples 209-231 that has a first section along the palm side of the thumb and a second section along the top of the thumb, wherein the first section and second section are stitched together along part of the length of the thumb facing the index and in part of the space between the thumb and index finger, and the stitching has a zig-zag pattern.

233. The glove of any of examples 209-231 that has a first section along the palm side of the thumb and a second section along the top of the thumb, wherein the first section and second section are stitched together along part of the length of the thumb facing the index and in part of the space between the thumb and index finger, and the stitching has a zig-zag pattern, and the stitching in part of the space between the thumb and index finger is formed in a zig-zag pattern.

234. The glove of any of examples 232-233 wherein each angle of the zig-zag pattern is between 50° and 70°.

235. The glove of any of examples 232-233 wherein each angle of the zig-zag pattern is 60°.

236. The glove of any of examples 232-233 wherein each angle of the zig-zag pattern is between 30° and 45°.

237. The glove of any of examples 232-233 wherein each angle of the zig-zag pattern is 30°.

238. The glove of any of examples 232-233 wherein a thread is used to provide the stitching and the thread is stretchable.

239. The glove of example 238 wherein the thread stretches to twice its relaxed length when two pounds or less of force are applied to it.

240. The glove of example 238 wherein the thread stretches to twice its relaxed length when one pound or less of force is applied to it.

241. The glove of example 238 wherein the thread stretches to twice its relaxed length when either: 1/32 or less pound, 1/16 pound, 1/8 pound or less, 1/4 pound or less, or one-half pound or less, of force is applied to it.

242. The glove of example 238 wherein the thread stretches to twice its relaxed length when five pounds or less of force are applied to it.

243. A glove that includes a plurality of layers wherein each layer is sufficiently connected to other layers to prevent slippage between layers during the use intended for the glove.

244. The glove of example 243 wherein at least one layer is sufficiently connected to the layer(s) surrounding it by raised dimples on the outer surface of each connected layer.

245. The glove of example 243 wherein at least one layer is sufficiently connected to the layer(s) surrounding it by raised dimples on the outer surface of one layer mating with depressions on an adjacent layer.

246. The glove of example 243 wherein at least one layer is sufficiently connected to the layer(s) surrounding it by raised ridges on each adjacent layer.

247. A glove that includes a first material and a second material wherein the second material stretches at least twice as much when a stretching force is applied to it as the first material stretches when the same force is applied.

248. The glove of example 247 wherein the second material stretches at least three times as much as the first material when the same stretching force is applied to each.

249. The glove of example 247 wherein the second material stretches at least four times as much as the first material when the same stretching force is applied to each.

250. The glove of example 247 wherein the second material stretches at least five times as much as the first material when the same stretching force is applied to each.

251. The glove of example 247 wherein the second material stretches at least ten times as much as the first material when the same stretching force is applied to each.

252. The glove of any of examples 247-251 wherein the second material is positioned on the dorsum of the hand behind the finger MCP joints.

253. The glove of any of examples 247-252 wherein the second material is positioned between the thumb and the index finger.

254. The glove of any of examples 247-253 wherein the second material is positioned at the center of the palm portion.

255. The glove of any of examples 247-254 wherein the second material is positioned at the base of the area between at least two fingers.

256. The glove of any of examples 247-255 wherein the second material is positioned at the base of the area between each of the fingers.

257. The glove of example 256 wherein the flexible material is positioned at the base of the area between each of the fingers.

258. The glove of any of examples 247-257 wherein the flexible material is positioned at least at one of the MCP joints.

259. The glove of any of examples 247-257 wherein the flexible material is positioned at a plurality of the MCP joints.

260. The glove of any of examples 247-257 wherein the flexible material is positioned at least at one of the PIP joints.

261. The glove of any of examples 247-257 wherein the flexible material is positioned at a plurality of the PIP joints.

262. The glove of any of examples 247-257 wherein the flexible material is positioned at least at one of the DIP joints.

263. The glove of any of examples 247-257 wherein the flexible material is positioned at a plurality of the DIP joints.

264. The glove of any of examples 247-263 wherein the flexible material is positioned at one or both of the thumb IP joint and DIP joint.

265. The glove of any of examples 247-264 that includes one or more tactile sensors along the palm and/or palm region of at least one digit.

266. The glove of any of examples 247-265 that includes one or more tactile sensors at one or more fingertip portions.

267. The glove of any of examples 247-266 that includes tactile sensors at each fingertip portion.

268. The glove of any of examples 247-267 that includes one or more tactile sensors at the palm side tip of the thumb portion.

269. The glove of any of examples 247-268 that includes one or more tactile sensors at one or more positions on the palm portion.

270. The glove of any of examples 247-269 that includes one or more portions of the palm side of at least one digit between (a) the MCP joint and PIP joint of the index finger, middle finger, ring finger or little finger, (b) the PIP joint and DIP joint of the index finger, middle finger, ring finger or little finger, and/or (c) the IP joint and DIP joint of the thumb.

271. The glove of example 270 that includes one or more tactile sensors between the MCP joint and PIP joint of at least one finger.

272. The glove of any of examples 270-271 that includes one or more tactile sensors between the PIP joint and DIP joint of at least one finger.

273. The glove of any of examples 270-272 that includes one or more tactile sensors between the thumb IP joint and DIP joint.
274. The glove of any of examples 270-273 that includes one or more tactile sensors between the MCP joint and PIP joint of each finger.
275. The glove of example 274 that includes one or more tactile sensors between the IP joint and DIP joint of the thumb.
276. The glove of any of examples 265-275 wherein each of the tactile sensors is at least twice as hard as the glove material surrounding it as measured on either the Shore A or Shore D scale.
277. The glove of any of examples 265-275 wherein each of the tactile sensors is at least three times as hard as the glove material surrounding it as measured on either the Shore A or Shore D scale.
278. The glove of any of examples 265-275 wherein each of the tactile sensors is at least four times as hard as the glove material surrounding it as measured on either the Shore A or Shore D scale.
279. The glove of any of examples 265-275 wherein each of the tactile sensors is at least five times as hard as the glove material surrounding it as measured on either the Shore A or Shore D scale.
280. The glove of any of examples 265-275 wherein each of the tactile sensors is at least ten times as hard as the glove material surrounding it as measured on either the Shore A or Shore D scale.
281. The glove of any of examples 265-280 wherein each of the tactile sensors are comprised of plastic and the glove material surrounding each tactile sensor is comprised of cloth, spandex or rubber.
282. The glove of any of examples 265-280 wherein each of the tactile sensors is comprised of metal.
283. The glove of example 282 wherein the metal is steel.
284. The glove of example 282 wherein the metal is stainless steel.
285. The glove of any of examples 265-280 wherein each of the tactile sensors is comprised of either plastic or metal.
286. The glove of any of examples 265-280 wherein at least one of the tactile sensors is comprised of cloth.
287. The glove of example 286 wherein each tactile sensor that is comprised of cloth is surrounded by one or more of (a) a second cloth, or (b) a natural or synthetic rubber.
288. The glove of any of examples 248-287 that has a first section along the palm side of the thumb and a second section along the top of the thumb, wherein the first section and second section are stitched together along part of the length of the thumb facing the index and in part of the space between the thumb and index finger, and the stitching has a zig-zag pattern.
289. The glove of any of examples 248-287 that has a first section along the palm side of the thumb and a second section along the top of the thumb, wherein the first section and second section are stitched together along part of the length of the thumb facing the index and in part of the space between the thumb and index finger, and the stitching in at least part of the space between the thumb and index finger is formed in a zig-zag pattern.
290. The glove of any of examples 288-289 wherein each angle of the zig-zag pattern is between 50° and 70°.
291. The glove of any of examples 288-289 wherein each angle of the zig-zag pattern is 60°.
292. The glove of any of examples 288-289 wherein each angle of the zig-zag pattern is between 30° and 45°.
293. The glove of any of examples 288-289 wherein each angle of the zig-zag pattern is 30°.
294. The glove of any of examples 288-292 wherein a thread is used to provide the stitching and the thread is stretchable.
295. The glove of example 294 wherein the thread stretches to twice its relaxed length when two pounds or less of force are applied to it.
296. The glove of example 294 wherein the thread stretches to twice its relaxed length when one pound or less of force is applied to it.
297. The glove of example 294 wherein the thread stretches to twice its relaxed length when one-half pound or less of force is applied to it.
298. The glove of example 294 wherein the thread stretches to twice its relaxed length when five pounds or less of force are applied to it.
299. The glove of any of examples 247-298 that includes a plurality of layers wherein each layer is sufficiently connected to other layers to prevent slippage between layers during the use intended for the glove.
300. The glove of example 299 wherein at least one layer is sufficiently connected to the layer(s) surrounding it by raised dimples on the outer surface of each connected layer.
301. The glove of example 299 wherein at least one layer is sufficiently connected to the layer(s) surrounding it by raised dimples on the outer surface of one layer mating with depressions on an adjacent layer.
302. The glove of example 301 wherein at least one layer is sufficiently connected to the layer(s) surrounding it by raised ridges on one layer being received in depressions in an adjacent layer.
303. The glove of any of examples 247-302 that further includes cladding on at least one flexible portion, the cladding being pieces of material attached to and harder than the flexible material.
304. The glove of example 303 wherein the cladding is on each portion of flexible material.
305. The glove of example 303 or 304 wherein the cladding comprises separate pieces of plastic or metal.
306. The glove of any of examples 303-305 wherein the cladding is at least: 3, or 5, or 10 times harder than the flexible material as measured on either the Shore A or Shore D scale.

Having thus described preferred embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

What is claimed is:

1. A glove, wherein at least one MCP joint portion of the glove is has a pre-formed angle of 10-55°.
2. The glove of claim 1, wherein at least two MCP joint portions of the glove are formed at a flex angle of 10-45°.
3. The glove of claim 1, wherein at least one MCP joint portion of the glove is has a pre-formed angle of 15-50°.
4. The glove of claim 1, wherein at least one MCP joint portion of the glove is has a pre-formed angle of 20-55°.

5. The glove of claim 1, wherein at least one PIP joint portion of the glove is formed at a flex angle of 5-25°.

6. The glove of claim 1, wherein at least two PIP joint portions of the glove are has a pre-formed angle of 5-25°.

7. The glove of claim 1, wherein at least one PIP joint portion of the glove is has a pre-formed angle of 10-35°.

8. The glove of claim 1, wherein at least one PIP joint portion of the glove is has a pre-formed angle of 15-40°.

9. The glove of claim 1, wherein at least one DIP joint portion of the glove is has a pre-formed angle of 5-25°.

10. The glove of claim 1, wherein at least two DIP joint portions of the glove are has a pre-formed angle of 5-25°.

11. The glove of claim 1, wherein at least one DIP joint portion of the glove is has a pre-formed angle of 10-30°.

12. The glove of claim 1, wherein at least one DIP joint portion of the glove is has a pre-formed angle of 15-40°.

13. The glove of claim 1, wherein the thumb MCP joint portion of the glove is has a pre-formed angle of 10-45°.

14. The glove of claim 1, wherein the thumb PIP joint portion of the glove is has a pre-formed angle of 20-50°.

15. A glove, wherein at least one PIP joint portion of the glove is has a pre-formed angle of 5-40°.

16. The glove of claim 15, wherein at least two PIP joint portions of the glove are has a pre-formed angle of 5-25°.

17. The glove of claim 15, wherein at least one PIP joint portion of the glove is has a pre-formed angle of 10-35°.

18. The glove of claim 15, wherein at least one PIP joint portion of the glove is has a pre-formed angle of 15-40°.

19. The glove of claim 15, wherein at least one DIP joint portion of the glove is has a pre-formed angle of 5-25°.

20. The glove of claim 15, wherein at least two DIP joint portions of the glove are has a pre-formed angle of 5-25°.

21. The glove of claim 15, wherein at least one DIP joint portion of the glove is has a pre-formed angle of 10-30°.

22. The glove of claim 15, wherein at least one DIP joint portion of the glove is has a pre-formed angle of 15-40°.

23. The glove of claim 15, wherein the thumb MCP joint portion of the glove is has a pre-formed angle of 10-45°.

24. The glove of claim 15, wherein the thumb PIP joint portion of the glove is has a pre-formed angle of 20-50°.

25. A glove, wherein at least one DIP joint portion of the glove is has a pre-formed angle of 5-25°.

26. The glove of claim 25, wherein at least two DIP joint portions of the glove are has a pre-formed angle of 5-25°.

27. The glove of claim 25, wherein at least one DIP joint portion of the glove is pre-formed at an angle of 10-30°.

28. The glove of claim 25, wherein at least one DIP joint portion of the glove is pre-formed at an angle of 15-40°.

29. The glove of claim 25, wherein the thumb MCP joint portion of the glove is pre-formed at an angle of 10-45°.

30. The glove of claim 25, wherein the thumb PIP joint portion of the glove is pre-formed at an angle of 20-50°.

31. A glove, wherein the MCP joint of the glove of the thumb is pre-formed at an angle of 10-45°.

32. The glove of claim 31, wherein the PIP joint portion of the glove of the thumb is pre-formed at an angle of 20°-50°.

* * * * *